(12) United States Patent
Li et al.

(10) Patent No.: US 12,286,473 B2
(45) Date of Patent: Apr. 29, 2025

(54) ANTI-IL-1β ANTIBODY AND PHARMACEUTICAL COMPOSITION THEREOF AND USE OF SAME

(71) Applicant: Akeso Biopharma, Inc., Guangdong (CN)

(72) Inventors: Baiyong Li, Guangdong (CN); Yu Xia, Guangdong (CN); Peng Zhang, Guangdong (CN); Zhongmin Maxwell Wang, Guangdong (CN)

(73) Assignee: Akeso Biopharma, Inc., Guangdong (CN)

( * ) Notice: Subject to any disclaimer, the term of this patent is extended or adjusted under 35 U.S.C. 154(b) by 1093 days.

(21) Appl. No.: 17/267,115

(22) PCT Filed: Aug. 13, 2019

(86) PCT No.: PCT/CN2019/100343
§ 371 (c)(1),
(2) Date: Feb. 9, 2021

(87) PCT Pub. No.: WO2020/034941
PCT Pub. Date: Feb. 20, 2020

(65) Prior Publication Data
US 2021/0179706 A1 Jun. 17, 2021

(30) Foreign Application Priority Data
Aug. 14, 2018 (CN) .......................... 201810920403.6

(51) Int. Cl.
| | | |
|---|---|---|
| C07K 16/00 | (2006.01) | |
| A61K 47/68 | (2017.01) | |
| A61P 19/02 | (2006.01) | |
| A61P 37/06 | (2006.01) | |
| C07K 16/24 | (2006.01) | |
| A61K 39/00 | (2006.01) | |

(52) U.S. Cl.
CPC ........ *C07K 16/245* (2013.01); *A61K 47/6845* (2017.08); *A61P 19/02* (2018.01); *A61P 37/06* (2018.01); *C07K 16/244* (2013.01); *A61K 2039/505* (2013.01); *C07K 2317/21* (2013.01); *C07K 2317/24* (2013.01); *C07K 2317/31* (2013.01); *C07K 2317/52* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,876,969 A * | 3/1999 | Fleer ........................ B65B 69/00 |
| 7,446,175 B2 | 11/2008 | Gram et al. |
| 7,491,392 B2 | 2/2009 | Gram et al. |
| 7,531,166 B2 | 5/2009 | Masat et al. |
| 7,541,033 B2 | 6/2009 | Dickinson et al. |
| 8,398,966 B2 | 3/2013 | Wu et al. |
| 8,889,130 B2 | 11/2014 | Kamath |
| 10,077,302 B2 | 9/2018 | Grabulovski et al. |
| 10,106,604 B2 | 10/2018 | Gram et al. |
| 10,344,085 B2 | 7/2019 | Dengl et al. |
| 10,730,938 B2 | 8/2020 | Bedoucha et al. |

FOREIGN PATENT DOCUMENTS

| | | |
|---|---|---|
| CN | 1395581 A | 2/2003 |
| CN | 1484652 A | 3/2004 |
| CN | 1745103 A | 3/2006 |
| CN | 1780855 A | 5/2006 |
| CN | 101678104 A | 3/2010 |
| CN | 102655880 A | 9/2012 |
| CN | 102775493 A | 11/2012 |
| CN | 103328511 A | 9/2013 |

(Continued)

OTHER PUBLICATIONS

Paul, Fundamental Immunology, 3rd Edition, 1993, pp. 292-295, Fv Structure and Diversity in Three Dimensions (Year: 1993).*
Bendig M. M. Methods: A Companion to Methods in Enzymology, 1995; 8:83-93 (Year: 1995).*
Kappell et al., Current Opinions in Biotechnology, vol. 3, p. 548-553, 1992. (Year: 1992).*
Wall et al., Theriogenology, vol. 45, p. 57-68, 1996. (Year: 1996).*
Houdebine et al. Comparative Immunology, Microbiology, and Infectious Diseases, vol. 32, p. 107-121, 2009. (Year: 2009).*

(Continued)

*Primary Examiner* — M Franco G Salvoza
*Assistant Examiner* — Estella M. Gustilo
(74) *Attorney, Agent, or Firm* — COOLEY LLP

(57) ABSTRACT

The present invention belongs to the field of immunology, and relates to an anti-IL-1β antibody and pharmaceutical composition thereof and use of the same. Specifically, the present invention relates to an anti-IL-1β antibody or an antigen-binding fragment thereof, wherein a heavy chain variable region of the antibody comprises HCDR1-HCDR3 with amino acid sequences set forth in SEQ ID NO: 17-SEQ ID NO: 19, respectively; and a light chain variable region of the antibody comprises LCDR1-LCDR3 set forth in SEQ ID NO: 20-SEQ ID NO: 22, respectively. The antibody disclosed herein can effectively bind to human IL-1B, block the binding of IL-1B to a receptor IL-1R1 thereof, and inhibit the activation of downstream signaling pathways of IL-1B; having the potential of being used for preparing a medicament for preventing and treating autoimmune diseases, cryopyrin-associated periodic syndromes in children and adults, systemic juvenile idiopathic arthritis, gouty arthritis, cardiovascular diseases or tumors.

21 Claims, 12 Drawing Sheets

Specification includes a Sequence Listing.

(56) References Cited

FOREIGN PATENT DOCUMENTS

| CN | 103554264 | A |   | 2/2014  |         |
|----|-----------|---|---|---------|---------|
| CN | 103596591 | A |   | 2/2014  |         |
| CN | 104870015 | A |   | 8/2015  |         |
| CN | 105324396 | A |   | 2/2016  |         |
| CN | 107074942 | A |   | 8/2017  |         |
| CN | 107474139 | A | * | 12/2017 | C07K 16/30 |
| CN | 110818793 | A |   | 2/2020  |         |
| JP | 2017534646 | A |  | 11/2017 |         |
| WO | WO-2016075034 | A1 | | 5/2016 |         |
| WO | WO-2016075037 | A1 | | 5/2016 |         |
| WO | WO-2021190553 | A1 | | 9/2021 |         |

OTHER PUBLICATIONS

Komenaka, I. et al. Immunotherapy for Melanoma. Clinics in dermatology 22.3 (2004): 251-265), specifically p. 257. (Year: 2004).*

Evans, T.R.J. et al. Vaccine therapy for cancer fact or fiction? QJM: An International Journal of Medicine, vol. 92, Issue 6, Jun. 1999, pp. 299-307. (Year: 1999).*

Cuzick J, Powles T, Veronesi U, Forbes J, Edwards R, Ashley S, Boyle P. Overview of the main outcomes in breast-cancer prevention trials. Lancet. Jan. 25, 2003;361(9354):296-300. (Year: 2003).*

Hernandez-Ledesma, B. et al. Lunasin, a Novel Seed Peptide for Cancer Prevention. Peptides (New York, N.Y.: 1980) 30.2 (2009): 426-430. (Year: 2009).*

Schiffman et al., The New England Journal of Medicine, Vo. 353, No. 20, p. 2101-2104, 2005. (Year: 2005).*

Rudikoff S. et al. Single amino acid substitution altering antigen-binding specificity. Proc Natl Acad Sci U S A. Mar. 1982;79(6):1979-83. (Year: 1982).*

Houdebine et al., Journal of Biotechnology, vol. 34, p. 269-287, 1994. (Year: 1994).*

Fangming, K., et al., "Construction, Expression, and Bio-activity Assay of an Anti-IL-1βscfv and TNFR1 Fusion Protein," Chinese Journal of Microbiology and Immunology, 32, Issue 10:855-860 (2012), with English Abstract on front page.

Marco et al., "Canakinumab treatment for patients with active recurrent or chronic TNFreceptor-associated periodic syndrome (TRAPS): an open-label, phase II study," Annals of the Rheumatic Diseases 76(1):173-178 (2017).

Alfthan et al., "Properties of a single-chain antibody containing different linker peptides," Protein Eng. 8(7):725-731 (1995).

Alten et al., "The human anti-IL-1β monoclonal antibody ACZ885 is effective in joint inflammation models in mice and in a proof-of-concept study in patients with rheumatoid arthritis," Arthritis Res Ther. 10:R67, pp. 1-9 (2008).

Alten R et al., "Efficacy and safety of the human anti-IL-1beta monoclonal antibody canakinumab in rheumatoid arthritis: results of a 12-week, phase II, dose-finding study," BMC Musculoskeletal Disorders. 12:153, 11 pages (2011).

Amaral et al., "NLRP3 inflammasome-mediated neutrophil recruitment and hypernociception depend on leukotriene B(4) in a murine model of gout, " Arthritis Rheum. 64(2):474-484 (2012).

Bird et al., "Single-chain antigen-binding proteins," Science 242:423-426 (1988).

Blum et al, et al., "Role of cytokines in heart failure," Am Heart J. 135:181-186 (1998).

Boraschi et al., "The family of the interleukin-1 receptors," Immunological Reviews. 281(1):197-232. (2018).

Lin et al., "New Insights into the Role of IL-1β in Experimental Autoimmune Encephalomyelitis and Multiple Sclerosis," J Immunol. 198(12): 4553-4560 (2017).

Choi et al. "Recombinant chimeric OKT3 scFv IgM antibodies mediate immune suppression while reducing T cell activation in vitro," Eur. J. Immunol. 31: 94-106 (2001).

Chothia & Lesk, "Canonical structures for the hypervariable regions of immunoglobulins," J Mal. Biol. 196:901-917 (1987).

Chothia et al., "Conformations of immunoglobulin hypervariable regions," Nature 342(6252):877-883 (1989).

Clark, "Antibody humanization: a case of the 'Emperor's new clothes?" Immunol. Today 21:397-402 (2000).

Coloma et al., "Design and production of novel tetravalent bispecific antibodies," Nature Biotechnology 15:159-163 (1997).

Cozzolino et al., "Interleukin 1 as an autocrine growth factor for acute myeloid leukemia cells," Proc Natl Acad Soci USA. 86(7):2369-2373 (1989).

Cumpelik et al., "Neutrophil microvesicles resolve gout by inhibiting C5a-mediated priming of the inflammasome," Ann Rheum Dis. doi: 10.1136/annrheumdis-2015-207338, pp. 1-11 (2015).

Dalekos et al., "Increased serum levels of interleukin-1β in the systemic circulation of patients with essential hypertension: Additional risk factor for atherogenesis in hypertensive patients?" J Lab Clin Med. 129:300-308 (1997).

De Benedetti et al., "Canakinumab for the Treatment of Autoinflammatory Recurrent Fever Syndromes," N Engl J Med. 378(20):1908-1919 (2018).

Di Giovine et al., "Interleukin 1 (IL 1) as a mediator of crystal arthritis. Stimulation of T cell and synovial fibroblast mitogenesis by urate crystal-induced IL 1.," J Immunol. 138: 3213-3218 (1987).

Dinarello et al., "The role of interleukin-1 in disease," N Engl J Med. 328: 106 (1993).

Fitzgerald et al., "Rational engineering of antibody therapeutics targeting multiple oncogene pathways," MAbs 3:299-309 (2011).

Genbank Accession No. p01834, dated Apr. 7, 2021, 6 pages.
Genbank Accession No. P01861.1, dated Apr. 7, 2021, 6 pages.
Genbank Accession No. P01857, dated Apr. 7, 2021, 9 pages.
GenBank ID: NP_000567.1, dated May 3, 2021, 4 pages.
GenBank ID: NP_000868, dated May 3, 2021, 4 pages.
GenBank ID: CAA42441.1, dated Oct. 7, 2008, 2 pages.

Ghivizzani et al., "Constitutive intra-articular expression of human IL-1 beta following gene transfer to rabbit synovium produces all major pathologies of human rheumatoid arthritis," J Immunol. 1:3604-12 (1997).

Gravallese et al., "Bone destruction in arthritis," Ann Rheum Dis. 61:84-86 (2002).

Gravallese EM et al., "Synovial tissue in rheumatoid arthritis is a source of osteoclast differentiation factor," Arthritis Rheum. 4(2)3:250-258 (2000).

Kone-Paut et al., "Real-World Experience and Impact of Canakinumab in Cryopyrin-Associated Periodic Syndrome: Results From a French Observational Study," Arthritis Care Res. (Hoboken); 69:903-911. (2017).

Holliger et al., "Diabodies": small bivalent and bispecific antibody fragments, Proc. Natl. Acad. Sci. USA 90(14): 6444-6448 (1993).

Horai et al., Development of chronic inflammatory arthropathy resembling rheumatoid arthritis in interleukin 1 receptor antagonist-deficient mice, J Exp Med. 191:313-20 (2000).

Hu et al., "Minibody: A novel engineered anti-carcinoembryonic antigen antibody fragment (single-chain Fv-CH3) which exhibits rapid, high-level targeting of xenografts," Cancer Res. 56:3055-3061 (1996).

Huston et al., "Protein engineering of antibody binding sites: recovery of specific activity in an anti-digoxin single-chain Fv analogue produced in *Escherichia coli*," Proc. Natl. Acad. Sci. USA 85:5879 5883 (1988).

International Search Report and Written Opinion issued by the International Searching Authority for Application No. PCT/CN2019/100343, dated Oct. 30, 2019, 30 pages, including English translation of Search Report.

International Preliminary Report on Patentability issued by the International Searching Authority for Application No. PCT/CN2019/100343, dated Feb. 16, 201, 5 pages.

Johnson et al., "Matrix metalloproteinases," Curr Opin Chem Biol. 2(4):466-471 (1998).

Jones et al., "Replacing the complementarity-determining regions in a human antibody with those from a mouse," Nature, 321:522-525 (1986).

Kapadia et al., "The Role of Cytokines in the Failing Human Heart," Cardiol Clin. 16(4):645 (1998).

(56) References Cited

OTHER PUBLICATIONS

Kipriyanov et al., "Bispecific tandem diabody for tumor therapy with improved antigen binding and pharmacokinetics," J. Mol. Biol. 293(1):41-56 (1999).
Kohler et al., Continuous cultures of fused cells secreting antibody of predefined specificity Nature, 256(5517):495-497(1975).
Kostelny et al. Formation of a bispecific antibody by the use of leucine zippers, J. Immunol. 148(5):1547-1553 (1992).
Li Lingqin et al., "Altered Expression if IL-1β in Peripheral Blood from Gout Patients and Its Association with Gouty Arthritis," Chinese Journal of General Practitioners. 14: 29-31 (2015).
Lyseng-Williamson et al., "Canakinumab: A guide to its use in acute gouty arthritis flares," BioDrugs. 27: 401-406 (2013).
Martinon et al., "Gout-associated uric acid crystals activate the NALP3 inflammasome," Nature. 440(7081):237-241 (2006).
Miller et al., "Stability engineering of scFvs for the development of bispecific and multivalent antibodies," Protein Eng Des Sel 23:549-557 (2010).
Müller et al., "Bispecific antibodies for cancer immunotherapy: Current perspectives," BioDrugs 24(2):89-98 (2010).
Nakazaki et al., "Preoperative and postoperative cytokines in patients with cancer," Cancer. 70(3):709-713 (1992).
Orrock et al., "Association of brain injury and neonatal cytokine response during therapeutic hypothermia in newborns with hypoxic-ischemic encephalopathy," Expert Rev Clin Pharmacol. 9:1015-24. (2016).
Poljak RJ et al., "Production and structure of diabodies," Structure 2:1121 1123 (1994).
Reichmann et al., "Reshaping human antibodies for therapy," Nature, 332(6162):323-329 (1988).
Ridker et al., "Antiinflammatory Therapy with Canakinumab for Atherosclerotic Disease," N Engl J Med. 377:1119-1131 (2017).
Ridker et al, "Effect of interleukin-1β inhibition with canakinumab on incident lung cancer in patients with atherosclerosis: exploratory results from a randomised, double-blind, placebo-controlled trial," Lancet. 390(10105):1833-1842 (2017).
Schlesinger et al., "Canakinumab reduces the risk of acute gouty arthritis flares during initiation of allopurinol treatment: results of a double-blind, randomised study," Ann Rheum Dis. 70(7):1264-1271 (2011).
So et al., "Canakinumab for the treatment of acute flares in difficult-to-treat gouty arthritis: Results of a multicenter, phase II, dose-ranging study," Arthritis & Rheum. 62(10):3064-3076(2010).
Songsivilai and Lachmann, "Bispecific antibody: a tool for diagnosis and treatment of disease.," Clin. Exp. Immunol. 79:315-321 (1990).
Strand V et al. Rheumatology (Oxford). 43:ili10-iii16 (2004).
Mertens et al., "Anakinra for rheumatoid arthritis: a systematic review," J Rheumatol. 36(6):1118-1125 (2009).
Sun et al., "Comparison of Systemic Juvenile Idiopathic Arthritis with Classical Auto-inflammatory Disease," Progress in Modern Biomedicine 8:1584-1588 (2016).
Takayanagi et al., "Involvement of receptor activator of nuclear factor kappaB ligand/osteoclast differentiation factor in osteoclastogenesis from synoviocytes in rheumatoid arthritis," Arthritis Rheum. 43(2):259-69 (2000).
Torres et al, "Hyperalgesia, synovitis and multiple biomarkers of inflammation are suppressed by interleukin 1 inhibition in a novel animal model of gouty arthritis," Ann Rheum Dis. 68(10):1602-1608 (2009).
van den Berg et al., "Pathogenesis of joint damage in rheumatoid arthritis: evidence of a dominant role for interleukin-I," Baillieres Best Pract Res Clin Rheumatol. 13(1):577-97(1999).
van Oostrum et al., "The structure of murine interleukin-1 beta at 2.8 A resolution," J Struct Biol. 107(2):189-95 (1991).
Woerner et al., "Complications of systemic juvenile idiopathic arthritis: risk factors and management recommendations," Expert Rev Clin Immunol. 11(5):575-88. (2015).
Wurster et al., "Periodic Fever syndromes," Pediatr Ann. 40(1):48-54. (2011).
Yndestad et al., "Role of inflammation in the progression of heart failure," Curr Cardiol Rep. 9:236-41 (2007).
Yokota et al., "Long-term safety and efficacy of canakinumab in cryopyrin-associated periodic syndrome: results from an open-label, phase III pivotal study in Japanese patients," Clin Exp Rheumatol. 35 Suppl 108(6):19-26. (2017).
Yue et al., "Cytokine expression increases in nonmyocytes from rats with postinfarction heart failure," Am J Physiol. 275(1 pt 2):H250-H258 (1998).
Brinkmann U. et al., "Cloning and Expression of the Recombinant Fab Fragment of Monoclonal Antibody K1 That Reacts with Mesothelin Present on Mesotheliomas and Ovarian Cancers," International Journal of Cancer, 1997, vol. 71, pp. 638-644.

\* cited by examiner

SEQUENCE LISTING

<160> NUMBER OF SEQ ID NOS: 26

<210> SEQ ID NO 1
<211> LENGTH: 354
<212> TYPE: DNA
<213> ORGANISM: Artificial Sequence
<220> FEATURE:
<223> OTHER INFORMATION: Nucleotide sequence of antibody 3H6 heavy
      chain variable region

<400> SEQUENCE: 1

| | | | | | |
|---|---|---|---|---|---|
| caggtgaccc | tgaaggagag | cggaccagga | atcctgcagc | ctagccagac | actgagcctg | 60 |
| acttgcagct | tcagcggctt | cagcctgagc | acaagcggaa | tgggcgtgtc | ttggatcagg | 120 |
| cagccatcag | gaaagggact | cgagtggctg | gctcacatct | actgggacga | cgacaagcgg | 180 |
| tacaacccct | ccctgaagag | caggctgacc | atcagcaagg | acaccagcag | caaccaggtg | 240 |
| ttcctgaaga | tcaccagcgt | ggacaccgcc | gatagcgcta | cctactattg | cgccagaagc | 300 |
| gcctactaca | gcttcgccta | ttggggccag | ggaacactgg | tgtccgtgtc | agcc | 354 |

<210> SEQ ID NO 2
<211> LENGTH: 118
<212> TYPE: PRT
<213> ORGANISM: Artificial Sequence
<220> FEATURE:
<223> OTHER INFORMATION: The amino acid sequence of antibody 3H6 heavy
      chain variable region

<400> SEQUENCE: 2

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Ser Ala Thr Tyr Tyr
                85                  90                  95

Cys Ala Arg Ser Ala Tyr Tyr Ser Phe Ala Tyr Trp Gly Gln Gly Thr
            100                 105                 110

Leu Val Ser Val Ser Ala
        115

<210> SEQ ID NO 3
<211> LENGTH: 318
<212> TYPE: DNA
<213> ORGANISM: Artificial Sequence
<220> FEATURE:
<223> OTHER INFORMATION: Nucleotide sequence of antibody 3H6 light chain
      variable region

<400> SEQUENCE: 3

| | | | | | |
|---|---|---|---|---|---|
| gatatcgtca | tgacacagtc | acataagttt | atgtctacta | gtgtgggcgg | cgggtcaga | 60 |
| attacctgta | aggcctctca | ggacgtggat | acagacgtgg | cttggttcca | gcagaagccc | 120 |
| ggacagagcc | ctaaactgct | gatctactgg | gcctccacaa | ggcacactgg | ggtgccagat | 180 |
| cggttcactg | gatcaggcag | cgggaccgac | tttactctga | ccatttccaa | cgtccagtct | 240 |

```
gaggatctgg ctgactattt ctgccagcag tacagctcct atcccacctt tggagcaggc    300
acaaagctgg aactgaaa                                                  318
```

<210> SEQ ID NO 4
<211> LENGTH: 106
<212> TYPE: PRT
<213> ORGANISM: Artificial Sequence
<220> FEATURE:
<223> OTHER INFORMATION: The amino acid sequence of antibody 3H6 light
      chain variable region

<400> SEQUENCE: 4

```
Asp Ile Val Met Thr Gln Ser His Lys Phe Met Ser Thr Ser Val Gly
1               5                   10                  15

Gly Arg Val Arg Ile Thr Cys Lys Ala Ser Gln Asp Val Asp Thr Asp
            20                  25                  30

Val Ala Trp Phe Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Thr
                85                  90                  95

Phe Gly Ala Gly Thr Lys Leu Glu Leu Lys
            100                 105
```

<210> SEQ ID NO 5
<211> LENGTH: 354
<212> TYPE: DNA
<213> ORGANISM: Artificial Sequence
<220> FEATURE:
<223> OTHER INFORMATION: Nucleotide sequence of antibody 3H6H1L1 heavy
      chain variable region

<400> SEQUENCE: 5

```
caggtgacac tgaaggagtc tggccccgcc ctgctgaagc ctacccagac actgaccctg    60
acatgtacct tctccggctt ttctctgagc acctccggca tgggcgtgtc ttggatcagg   120
cagccaagcg gcaaggccct ggagtggctg gcacacatct actgggacga tgacaagcgg   180
tataacccct ccctgaagtc tagactgaca atctctaagg ataccagctc caaccaggtg   240
ttcctgaaga tcacaaatgt ggataccgtg gacacagcca cctactattg cgcccggagc   300
gcctactatt cctttgccta ctggggccag ggcacactgg tgtctgtgag cgcc          354
```

<210> SEQ ID NO 6
<211> LENGTH: 118
<212> TYPE: PRT
<213> ORGANISM: Artificial Sequence
<220> FEATURE:
<223> OTHER INFORMATION: The amino acid sequence of antibody 3H6H1L1
      heavy chain variable region

<400> SEQUENCE: 6

```
Gln Val Thr Leu Lys Glu Ser Gly Pro Ala Leu Leu Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Ser Gly Lys Ala Leu Glu
        35                  40                  45
```

Trp Leu Ala His Ile Tyr Trp Asp Asp Asp Lys Arg Tyr Asn Pro Ser
 50                  55                  60

Leu Lys Ser Arg Leu Thr Ile Ser Lys Asp Thr Ser Ser Asn Gln Val
 65                  70                  75                  80

Phe Leu Lys Ile Thr Asn Val Asp Thr Val Asp Thr Ala Thr Tyr Tyr
                 85                  90                  95

Cys Ala Arg Ser Ala Tyr Tyr Ser Phe Ala Tyr Trp Gly Gln Gly Thr
            100                 105                 110

Leu Val Ser Val Ser Ala
        115

<210> SEQ ID NO 7
<211> LENGTH: 318
<212> TYPE: DNA
<213> ORGANISM: Artificial Sequence
<220> FEATURE:
<223> OTHER INFORMATION: Nucleotide sequence of antibody 3H6H1L1 light
      chain variable region

<400> SEQUENCE: 7
gatatccaga tgacccagtc ccacagctcc atgtccacat ctgtgggcga ccgggtgaga     60
atcacctgtc gggcctccca ggacgtggat acagacgtgg cctggtttca gcagaagccc    120
ggccaggccc ctaagctgct gatctactgg gccagcacca ggcactccgg agtgccatct    180
cgcttcagcg gctccggctc tggcacagac ttcaccctga caatcagcaa cgtgcagcca    240
gaggatttcg ccgactacta ttgccagcag tactctagct atcccacctt tggcgccggc    300
acaaagctgg agctgaag                                                  318

<210> SEQ ID NO 8
<211> LENGTH: 106
<212> TYPE: PRT
<213> ORGANISM: Artificial Sequence
<220> FEATURE:
<223> OTHER INFORMATION: The amino acid sequence of antibody 3H6H1L1
      light chain variable region

<400> SEQUENCE: 8

Asp Ile Gln Met Thr Gln Ser His Ser Ser Met Ser Thr Ser Val Gly
 1               5                  10                  15

Asp Arg Val Arg Ile Thr Cys Arg Ala Ser Gln Asp Val Asp Thr Asp
             20                  25                  30

Val Ala Trp Phe Gln Gln Lys Pro Gly Gln Ala Pro Lys Leu Leu Ile
         35                  40                  45

Tyr Trp Ala Ser Thr Arg His Ser Gly Val Pro Ser Arg Phe Ser Gly
 50                  55                  60

Ser Gly Ser Gly Thr Asp Phe Thr Leu Thr Ile Ser Asn Val Gln Pro
 65                  70                  75                  80

Glu Asp Phe Ala Asp Tyr Tyr Cys Gln Gln Tyr Ser Ser Tyr Pro Thr
                 85                  90                  95

Phe Gly Ala Gly Thr Lys Leu Glu Leu Lys
            100                 105

<210> SEQ ID NO 9
<211> LENGTH: 354
<212> TYPE: DNA
<213> ORGANISM: Artificial Sequence
<220> FEATURE:
<223> OTHER INFORMATION: Nucleotide sequence of antibody 3H6H2L2 heavy
      chain variable region

<400> SEQUENCE: 9

```
caggtgacac tgaaggagtc cggccccgcc ctggtgaagc ctacccagac actgaccctg    60
acatgtacct tcagcggctt ttctctgagc acctccggca tgggcgtgtc ctggatcagg   120
cagccatctg gcaaggccct ggagtggctg gcccacatct actgggacga tgacaagcgg   180
tattctccca gcctgaagtc tagactgaca atcagcaagg ataccagctc caaccaggtg   240
ttcctgacaa tcaccaacgt ggaccccgtg gacacagcca cctactattg cgcccggagc   300
gcctactatt cctttgccta ctggggccag ggcacactgg tgtccgtgtc tgcc         354
```

<210> SEQ ID NO 10
<211> LENGTH: 118
<212> TYPE: PRT
<213> ORGANISM: Artificial Sequence
<220> FEATURE:
<223> OTHER INFORMATION: The amino acid sequence of antibody 3H6H2L2 heavy chain variable region

<400> SEQUENCE: 10

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Ser Gly Lys Ala Leu Glu
        35                  40                  45

Trp Leu Ala His Ile Tyr Trp Asp Asp Asp Lys Arg Tyr Ser Pro Ser
    50                  55                  60

Leu Lys Ser Arg Leu Thr Ile Ser Lys Asp Thr Ser Ser Asn Gln Val
65                  70                  75                  80

Phe Leu Thr Ile Thr Asn Val Asp Pro Val Asp Thr Ala Thr Tyr Tyr
                85                  90                  95

Cys Ala Arg Ser Ala Tyr Tyr Ser Phe Ala Tyr Trp Gly Gln Gly Thr
            100                 105                 110

Leu Val Ser Val Ser Ala
        115

<210> SEQ ID NO 11
<211> LENGTH: 318
<212> TYPE: DNA
<213> ORGANISM: Artificial Sequence
<220> FEATURE:
<223> OTHER INFORMATION: Nucleotide sequence of antibody 3H6H2L2 light chain variable region

<400> SEQUENCE: 11

```
gatatccaga tgacacagag ccctagctcc ctgagcgcct ccgtgggcga ccgggtgaga    60
atcacctgta gggcctctca ggacgtggat acagacgtgg cctggtacca gcagaagccc   120
ggcaaggccc ctaagctgct gatctattgg gcctctaccc tgcagagcgg agtgccatcc   180
cggttctctg gcagcggctc cggaacagac ttcaccctga caatctctag cctgcagcca   240
gaggacttcg ccacctacta ttgccagcag tactcctctt atcccacctt tggcgccggc   300
acaaagctgg agctgaag                                                 318
```

<210> SEQ ID NO 12
<211> LENGTH: 106
<212> TYPE: PRT
<213> ORGANISM: Artificial Sequence
<220> FEATURE:
<223> OTHER INFORMATION: The amino acid sequence of antibody 3H6H2L2 light chain variable region

<400> SEQUENCE: 12

Asp Ile Gln Met Thr Gln Ser Pro Ser Ser Leu Ser Ala Ser Val Gly
1               5                   10                  15

Asp Arg Val Arg Ile Thr Cys Arg Ala Ser Gln Asp Val Asp Thr Asp
            20                  25                  30

Val Ala Trp Tyr Gln Gln Lys Pro Gly Lys Ala Pro Lys Leu Leu Ile
        35                  40                  45

Tyr Trp Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Thr
                85                  90                  95

Phe Gly Ala Gly Thr Lys Leu Glu Leu Lys
            100                 105

<210> SEQ ID NO 13
<211> LENGTH: 354
<212> TYPE: DNA
<213> ORGANISM: Artificial Sequence
<220> FEATURE:
<223> OTHER INFORMATION: Nucleotide sequence of antibody 3H6H3L3 heavy
      chain variable region

<400> SEQUENCE: 13
caggtgacac tgaaggagag cggcccagcc ctggtgaagc caacccagac actgaccctg      60
acatgtacct tctccggctt tagcctgtcc acctctggca tgggcgtgtc ttggatcagg     120
cagccacctg gcaaggccct ggagtggctg gccctgatct actgggacga tgacaagcgg     180
tatagccctt ccctgaagag cagactgaca atctccaagg atacctctaa gaaccaggtg     240
gtgctgacaa tcaccaacgt ggaccccgtg gacacagcca cctactattg cgcccggagc     300
gcctactatt cctttgccta ctggggccag ggcacactgg tgtctgtgag cgcc           354

<210> SEQ ID NO 14
<211> LENGTH: 118
<212> TYPE: PRT
<213> ORGANISM: Artificial Sequence
<220> FEATURE:
<223> OTHER INFORMATION: The amino acid sequence of antibody 3H6H3L3
      heavy chain variable region

<400> SEQUENCE: 14

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Ser Lys Asp Thr Ser Lys Asn Gln Val
65                  70                  75                  80

Val Leu Thr Ile Thr Asn Val Asp Pro Val Asp Thr Ala Thr Tyr Tyr
                85                  90                  95

Cys Ala Arg Ser Ala Tyr Tyr Ser Phe Ala Tyr Trp Gly Gln Gly Thr
            100                 105                 110

```
<210> SEQ ID NO 15
<211> LENGTH: 318
<212> TYPE: DNA
<213> ORGANISM: Artificial Sequence
<220> FEATURE:
<223> OTHER INFORMATION: Nucleotide sequence of antibody 3H6H3L3 light
      chain variable region

<400> SEQUENCE: 15
gatatccaga tgacacagag ccctagctcc ctgagcgcct ccgtgggcga cagggtgacc      60
atcacatgta gagcctctca ggacgtggat accgacctgg cctggtacca gcagaagccc     120
ggcaaggccc ctaagctgct gatctattgg gcctctaccc tgcagagcgg agtgccatcc     180
cggttctctg gcagcggctc cggaacagac ttcaccctga caatctctag cctgcagcca     240
gaggacttcg ccacctacta ttgccagcag tactcctctt atcccacctt tggcgccggc     300
acaaagctgg agctgaag                                                   318

<210> SEQ ID NO 16
<211> LENGTH: 106
<212> TYPE: PRT
<213> ORGANISM: Artificial Sequence
<220> FEATURE:
<223> OTHER INFORMATION: The amino acid sequence of antibody 3H6H3L3
      light chain variable region

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Asp
            20                  25                  30

Leu Ala Trp Tyr Gln Gln Lys Pro Gly Lys Ala Pro Lys Leu Leu Ile
        35                  40                  45

Tyr Trp Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Thr
                85                  90                  95

Phe Gly Ala Gly Thr Lys Leu Glu Leu Lys
            100                 105

<210> SEQ ID NO 17
<211> LENGTH: 10
<212> TYPE: PRT
<213> ORGANISM: Artificial Sequence
<220> FEATURE:
<223> OTHER INFORMATION: HCDR1

<400> SEQUENCE: 17

Gly Phe Ser Leu Ser Thr Ser Gly Met Gly
1               5                   10

<210> SEQ ID NO 18
<211> LENGTH: 7
<212> TYPE: PRT
<213> ORGANISM: Artificial Sequence
<220> FEATURE:
<223> OTHER INFORMATION: HCDR2
```

Leu Val Ser Val Ser Ala
        115

```
<400> SEQUENCE: 18

Ile Tyr Trp Asp Asp Lys
1               5

<210> SEQ ID NO 19
<211> LENGTH: 10
<212> TYPE: PRT
<213> ORGANISM: Artificial Sequence
<220> FEATURE:
<223> OTHER INFORMATION: HCDR3

<400> SEQUENCE: 19

Ala Arg Ser Ala Tyr Tyr Ser Phe Ala Tyr
1               5                   10

<210> SEQ ID NO 20
<211> LENGTH: 6
<212> TYPE: PRT
<213> ORGANISM: Artificial Sequence
<220> FEATURE:
<223> OTHER INFORMATION: LCDR1

<400> SEQUENCE: 20

Gln Asp Val Asp Thr Asp
1               5

<210> SEQ ID NO 21
<211> LENGTH: 3
<212> TYPE: PRT
<213> ORGANISM: Artificial Sequence
<220> FEATURE:
<223> OTHER INFORMATION: LCDR2

<400> SEQUENCE: 21

Trp Ala Ser
1

<210> SEQ ID NO 22
<211> LENGTH: 8
<212> TYPE: PRT
<213> ORGANISM: Artificial Sequence
<220> FEATURE:
<223> OTHER INFORMATION: LCDR3

<400> SEQUENCE: 22

Gln Gln Tyr Ser Ser Tyr Pro Thr
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: REPEAT
<222> LOCATION: (1)..(5)
<223> OTHER INFORMATION: Repeat for m, wherein m is a positive integer

<400> SEQUENCE: 23

Gly Gly Gly Gly Ser
1               5

<210> SEQ ID NO 24
<211> LENGTH: 7
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: REPEAT
<222> LOCATION: (3)..(7)
<223> OTHER INFORMATION: repeat for n, wherein n is a positive integer

<400> SEQUENCE: 24

Ser Ser Gly Gly Gly Gly Ser
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct

<400> SEQUENCE: 25

Gly Gly Gly Gly Ser
1               5

<210> SEQ ID NO 26
<211> LENGTH: 20
<212> TYPE: PRT
<213> ORGANISM: Artificial Sequence
<220> FEATURE:
<223> OTHER INFORMATION: Synthetic Construct

<400> SEQUENCE: 26

Gly Gly Gly Gly Ser Gly Gly Gly Gly Ser Gly Gly Gly Gly Ser Gly
1               5                   10                  15

Gly Gly Gly Ser
            20
```

ANTI-IL-1β ANTIBODY AND PHARMACEUTICAL COMPOSITION THEREOF AND USE OF SAME

RELATED APPLICATIONS

This application is a U.S. National Phase Application, filed under 35 U.S.C. § 371, of International Application No. PCT/CN2019/100343, filed on Aug. 13, 2019, which claims priority to, and the benefit of, Chinese Application No. 201810920403.6, filed on Aug. 14, 2018. The contents of each of the aforementioned patent applications are incorporated herein by reference in their entireties.

SEQUENCE LISTING

The instant application contains a Sequence Listing which has been submitted in ASCII format via EFS-Web and is hereby incorporated by reference in its entirety. The ASCII copy, created on Aug. 21, 2024, is named "AKSO-006_SeqList.txt" and is about 16,405 bytes in size.

TECHNICAL FIELD

The present invention belongs to the field of immunology, and relates to an anti-IL-1B antibody, a pharmaceutical composition thereof and use of the same. Specifically, the present invention relates to an anti-human IL-1β antibody; more specifically, the present invention relates to an anti-human IL-1β monoclonal antibody; and furthermore specifically, the present invention relates to an anti-human IL-1β humanized monoclonal antibody.

BACKGROUND

Interleukin-1 (IL-1) family consists of two pro-inflammatory factors (IL-1a and IL-1B) and an IL-1 receptor antagonist (IL-1Ra), in which the IL-1α and IL-1β can effectively activate IL-1 receptors, and the IL-1Ra can adhere to the surface of the IL-1 receptors to block signaling. IL-1β is synthesized primarily by monocytes and macrophages. When cleaved by caspase-1, the IL-1β precursor protein can be activated. There are multiple ligand subtypes, including IL-1R1, IL-1R2, IL-1R3 (also known as IL-1 receptor accessory protein or IL-1RAcP), IL-1R4, IL-1R5, IL-1R6, IL-1R7, IL-1R8, IL-18BP, and 2 orphan receptors (IL-1R9 and IL-1R 10), in the IL-1 receptor family.

Recently, IL-1β has been found to be capable of binding to IL-1R1 and IL-1R2. IL-1R1 (also known as type 1 IL-1 receptor or IL-1R1) is a transmembrane receptor, which binds to IL-1β and IL-IRAcP to form a receptor complex, activating a related downstream intracellular signaling pathway and mediating IL-1β related biological effects. IL-1R2 has a higher affinity for IL-1β than IL-1R1; however IL-1R2 can't activate the related intracellular signaling pathway after binding to IL-1β due to its shorter intracellular segment. Both IL-1R1 and IL-1R2 can exist in a soluble form (Boraschi et al. *Immunological Reviews*. 281:197-232. (2018)).

IL-1β regulates the recruitment and activation of effector cells involved in innate and adaptive immunities, and is also involved in the pathogenesis of chronic diseases including gouty arthritis; various autoimmune diseases such as rheumatoid arthritis, multiple sclerosis, and periodic fever syndrome, and autoinflammatory diseases such as systemic juvenile idiopathic arthritis; as well as occurrence of diseases like cryopyrin-associated periodic syndromes in children and adults. The IL-1β pathway has recently been confirmed to be involved in the occurrence of tumors such as acute myeloid leukemia, liver cancer, lung cancer, and cardiovascular and cerebrovascular diseases, and drugs targeting IL-1β have shown good therapeutic and prophylactic effects (Cozzolino F et al. *Proc Natl Acad* Soci USA. 86:2369 (1989); Nakazaki H et al. *Cancer.* 70 (3): 709 (1992); Ridker P M et al. *Lancet.* 390 (10105): 1833-1842 (2017)).

Rheumatoid arthritis (RA) is a chronic and systemic autoimmune disease with joint lesion predominating. IL-1β plays a key role in the onset of RA. High level of IL-1β is present in the synovial fluid of RA patients (van den Berg et al. *Baillieres Best Pract Res Clin Rheumatol.* 13:577-97 (1999)), and IL-1β mediates leukocyte infiltration and secretion of matrix metalloproteinases in the joints, induces cartilage degradation and inhibits new cartilage matrix synthesis, thus leading to joint destruction (van den Berg et al. *Baillieres Best Pract Res Clin Rheumatol.* 13:577-97 (1999); Johnson L L et al. *Curr Opin Chem Biol.* 2:466-471 (1998)). In RA patients, IL-1β stimulates the differentiation and activation of osteoclasts, and is involved in the occurrence of bone erosion in RA-affected joints (Gravallese E M et al. *Ann Rheum Dis.* 61: ii 84-86 (2002); Ghivizzani S C et al. *J Immunol.* 1:3604-12 (1997); Horai R et al. *J Exp Med.* 191:313-20 (2000); Gravallese E M et al. *Arthritis Rheum.* 43:250-8 (2000); Takayanagi H et al. *Arthritis Rheum.* 43:259-69 (2000)). In addition, IL-1β promotes bone loss as well as leukocyte infiltration and pannus tissue formation in the synovium by regulating pathways involving TNF-α and IL-6 (Strand V et al. Rheumatology (Oxford). 43: iii10-iii16 (2004)). Clinical studies have demonstrated that the IL-1β antagonist significantly alleviates physical signs and symptoms of RA (Mertens M et al. *J Rheumatol.* 36 (6): 1118-25 (2009)), and anti-human IL-1β mAb Canakinumab (Ilaris®) significantly reduces disease activities in RA patients (Alten R et al. *Arthritis Res Ther.* 10: R67 (2008); Alten R et al. BMC Musculoskeletal Disorders. 12:153 (2011)).

Gout is a crystal-related arthropathy caused by the deposition of monosodium urate, which directly relates to hyperuricemia caused by the disorder of purine metabolism and/or the reduction of uric acid excretion, and particularly refers to acute characteristic arthritis and chronic gout stone disease, mainly including acute-onset arthritis, tophus formation, tophus chronic arthritis, urate nephropathy and uric acid lithangiuria, even joint disability and renal insufficiency in severe cases. Gout is often accompanied by abdominal obesity, hyperlipidemia, hypertension, type-2 diabetes, cardiovascular disease, etc. IL-1β is a factor driving the development of gout inflammation (Cumpelik A et al. *Ann Rheum Dis*. pii: annrheumdis-2015-207338 (2015)). A study has shown that in patients with gouty arthritis, the expressions of both IL-1β mRNA of a single mononuclear cell and serum IL-1β in peripheral blood are remarkably higher than those of the healthy control group, and those of the acute phase group are remarkably higher than those of the chronic phase group and the intermittent phase group; the concentration of serum IL-1β is positively correlated with indicators such as white blood cell, neutrophile granulocyte and erythrocyte sedimentation rate, suggesting that IL-1β may be involved in both acute and chronic gouty arthritis, and is also correlated with the degree of inflammation; and the concentration of serum IL-1β in the intermittent phase group is remarkably higher than that in the healthy control group, suggesting that the inflammation of joints and tissues may still exist although the symptoms of the joints disappear (Li Lingqin et al. *Chinese Journal of General Practitioners.* 14:29-31

(2015)). An animal experiment has shown that IL-1β plays an important role in both acute and chronic gouty arthritis, and urate crystals stimulate mononuclear cells and phagocytes in blood and synovial fluid to cause large release of IL-1β (Di Giovine F S et al. *J Immunol.* 138:3213-3218 (1987)). In a mouse model experiment, it was found that the IL-1β blocker can prevent neutrophil aggregation caused by intraperitoneal injection of urate crystals and aggregation is absent at sites lacking of IL-1β receptors in mice (Martinon F et al. *Nature.* 440:237-241 (2006)). Clinical studies have shown that IL-1β induces the production of a large number of pro-inflammatory cytokines during the acute gout attack (Amaral F A et al. *Arthritis Rheum.* 64:474-484 (2012); Torres R et al. *Ann Rheum Dis.* 68:1602-1608 (2009)).

In a clinical trial for evaluating the efficacy and safety of gout treatment, it was found that the anti-human IL-1β monoclonal antibody canakinumab can effectively alleviate clinical symptoms such as pain of patients with refractory gouty arthritis, obviously reduces the recurrence of gout compared with triamcinolone acetonide, and improves the quality of life (So A et al. *Arthritis Rhum.* 62:3064-3076 (2010)). In another clinical study, it was found that the anti-human IL-1β monoclonal antibody canakinumab can significantly reduce the number of gout attacks compared with colchicine (Schlesinger N et al. *Ann Rheum Dis.* 70:1264-1271 (2011)). The mAb canakinumab has currently been approved by the European Medicines Agency for the treatment of patients who are suffering from frequent gouty arthritis attacks and fail to tolerate or respond to nonsteroidal anti-inflammatory drugs, colchicine and glucocorticoids (Lyseng-Williamson K A et al. *BioDrugs.* 27:401-406 (2013)). The above studies suggest that the anti-IL-1β antibody can treat gout, alleviate symptoms and reduce recurrence more effectively compared with the existing treatments, exerting potential prophylaxis and treatment effects on the gout attack.

Multiple sclerosis is a chronic demyelinating disease mediated primarily by T cells of Th1 and Th17 subsets. Interleukin IL-1 family factors are very important for development of multiple sclerosis. IL-1 promotes the disease progression by accelerating the growth of T cells of Th17 subset, and also leads to the distribution of the chemokine CXCL12 in cerebral vessels from a normal location at the parenchyma to both sides of the endothelium until a depolarizing distribution is achieved, resulting in the vascular leakage and the entry of T cells into the brain parenchyma during the early disease progression (Chih-Chung Lin et al. *J Immunol.* 198:4553-4560 (2017)). Animal studies have demonstrated that experimental autoimmune encephalomyelitis (EAE) is not induced in IL-1 or IL-1R1 deficient mice, and the treatment with IL-1β inhibitors can delay the onset, reduce the severity, and shorten the duration of EAE in wild-type mice (Chih-Chung Lin et al. *J Immunol.* 198: 4553-4560 (2017)).

Recent clinical studies have also found that anti-IL-1β antibodies exert anti-inflammatory effects by antagonizing the IL-1β pathway, significantly reducing the risk of cardiovascular disease. Atherosclerosis and thrombosis are the pathological basis of coronary heart disease (Dalek os G N et al. *J Lab Clin Med.* 129:300 (1997)). In the rabbit model of high cholesterol and atherosclerosis, it was found that the expressions of IL-1β and IL-1β mRNA are elevated in lipid plaques, and reducing the IL-1 synthesis can delay the atherosclerosis progression (Dinarell o C A et al. *N Engl J Med.* 328:106 (1993)). The level of IL-1β increases during myocardial infarction, and the expression of IL-1β increases in both plasma and local myocardial infarction site during post-infarction myocardial remodeling, suggesting that IL-1β is involved in the occurrence and progression of myocardial hypertrophy, myocardial fibrosis, and insufficiency following myocardial infarction (Yue P et al. *Am J Physiol.* 275 (1Pt2): H250 (1998)). Heart failure is a complex syndrome, and according to studies, level increase of IL-1 occurs in the circulating blood of patients with congestive heart failure (Blum A et al. *Am Heart J.* 135 (2 Part 1): 181 (1998); Kapadia S et al. *Cardiol Clin.* 16 (4): 645 (1998)). IL-1β may be involved in the occurrence and progression of congestive heart failure caused by the increased chronic load; the level of serum IL-1β is markedly elevated in patients with grade III-IV heart failure, promoting the progression of congestive heart failure (Yndestad A et al. *Curr Cardiol Rep.* 9:236-41 (2007)). A phase III CANTOS clinical study evaluating the efficacy, safety and tolerability of the anti-human IL-1β antibody canakinumab against previous myocardial infarction combined with inflammatory atherosclerotic cardiovascular disease has shown that the anti-IL-1β antibody in combination with the standard treatment significantly reduces the incidence of cardiac death, non-fatal myocardial infarction and non-fatal cerebralvascular accident in patients (Ridker P M et al. *N Engl J Med.* 377:1119-1131 (2017)).

Another analysis of the CANTOS clinical study cohort for the anti-human IL-1β antibody canakinumab has found that the anti-IL-1β antibody canakinumab significantly reduces the risk of occurrence and death of lung cancer (Ridker P M et al. 390 (10105): 1833-1842 (2017)) *Lancet.* In an in vitro culture of acute myeloid leukemia (AML) cells from patients, it was found that the expression of IL-1 is elevated in more than 80% of primary AML patients, and IL-1β can significantly promote the tumor cell growth, while anti-IL-1β or IL-1α antibodies are effective in inhibiting the tumor cell growth (Cozzolino F et al. *Proc Natl Acad Soci USA.* 86:2369 (1989)). In patients with hepatocellular carcinoma, the level of IL-1 in serum is significantly increased compared with the healthy control group (Nakazaki H et al. *Cancer.* 70 (3): 709 (1992)).

Cryopyrin-associated periodic syndromes (CAPS) in children and adults are a rare disease caused by the overproduction of IL-1β due to a single gene mutation, resulting in weakness, flushing, fever, headache, arthralgia and conjunctivitis, which may occur in neonates or infants, may occur daily throughout the life of the patient, and may cause severe diseases and be potentially fatal in the long term, including deafness, bone and joint deformities, blindness due to central nervous system injury, and renal failure and premature death due to amyloidosis. The CAPS in children and adults include familial cold auto-inflammatory syndrome (FCAS), Muckle-Wells syndrome (MWS), neonatal-onset multisystem inflammatory disease, chronic infantile neurological cutaneous and articular syndrome, and familial cold urticaria. The anti-human IL-1β antibody canakinumab can significantly ameliorate clinical symptoms in patients with cryopyrin-associated periodic syndromes (Yokota S et al. *Clin Exp Rheumatol.* 35 Suppl 108 (6): 19-26. (2017); Kone-Paut I et al. Arthritis Care Res. (Hoboken); 69:903-911. (2017)), thereby being approved for treating cryopyrin-associated periodic syndromes (CAPS) in children (≥4 years old) and adults by Food and Drug Administration (FDA) and European Medicines Agency (EMA).

Periodic fever syndromes are a group of rare autoimmune diseases that lead to recurrent and persistent severe fever and pathogenic inflammation by non-infectious activation of the immune system, often lead to disability, and may be accompanied by arthralgia, swelling, myalgia, rash and fatal complications (Wurster V M et al. *Pediatr Ann.* 40 (1): 48-54. (2011)). Periodic fever syndromes include TNF receptor-associated periodic syndrome (TRAPS), hyper-IgD syndrome (HIDS)/mevalonate kinase deficiency (MKD), and familial mediterranean fever (FMF). Clinical studies have demonstrated that anti-human IL-1β mAb canakinumab can be effective in treating periodic fever syndromes (De Benedetti F et al. *N Engl J Med.* 378 (20): 1908-1919 (2018)). Therefore, the anti-human IL-1β mAb canakinumab was approved for treating periodic fever syndromes by FDA and the like.

Systemic juvenile idiopathic arthritis (sJIA) is a unique subtype in juvenile idiopathic arthritis, which mostly starts with the extra-articular manifestations such as long-term hyperpyrexia, rash, and anemia. It is commonly found in children aged 0-5 years, mainly features chronic arthromeningitis and is mostly accompanied by organ and tissue damages of different degrees. Its main manifestations are fever, rash, and arthralgia, and it has poor prognosis such as low long-term remission rate, high dysfunction rate and disability rate, and high mortality rate. (Woerner A et al. *Expert Rev Clin Immunol.* 11 (5): 575-88. (2015)). It is generally accepted that the sJIA is an autoinflammatory disease instead of an autoimmune disease (Sun Juan et al. *Progress in Modern Biomedicine.* 8:1584-1588 (2016)). Clinical studies have demonstrated that the anti-human IL-1β monoclonal antibody canakinumab can effectively treat active sJIA accompanied by fever and reduce steroid doses, and significantly reduces the recurrence of sJIA (Orrock J E et al. *Expert Rev Clin Pharmacol.* 9:1015-24. (2016)). Therefore the anti-IL-1β monoclonal antibody canakinumab is approved for treating systemic juvenile idiopathic arthritis by FDA and the like.

There is still a need to develop new anti-IL-1β antibodies.

SUMMARY OF THE INVENTION

After intensive study and creative effort, the inventors used mammalian cell expression systems to express recombinant IL-1β-His as an antigen to immunize mice, and obtained hybridoma cells by fusion of mouse spleen cells and myeloma cells. The inventors acquired the following hybridoma cell line by screening a large number of the samples:

the hybridoma cell line LT010 deposited at China Center for Type Culture Collection (CCTCC) on Jun. 21, 2018 with an accession number of CCTCC NO: C2018133.

The inventors surprisingly found:

the hybridoma cell line LT010 may secrete and produce a specific monoclonal antibody (named as 3H6) that specifically binds to human IL-1B, and the monoclonal antibody can block the binding of IL-1β to IL-1R1 very effectively;

Furthermore, the inventors creatively prepared anti-human IL-1β humanized antibodies (respectively named as 3H6H1L1, 3H6H2L2, 3H6H3L3, and 3H6H4L1), all of which may bind to the human IL-1β effectively, block the binding of IL-1β to a receptor thereof (IL-1R1), and inhibit the activation of a downstream signaling pathway of IL-1B. And these anti-human IL-1β humanized antibodies have the potential of being used in preparing medicaments for reducing, preventing or treating diseases such as rheumatoid arthritis, gout, multiple sclerosis, cardiovascular events and/or cardiovascular diseases, tumors, cryopyrin-associated periodic syndromes in children and adults, periodic fever syndromes, and systemic juvenile idiopathic arthritis.

The present invention is detailed below.

One aspect of the present invention relates to an anti-IL-1β antibody or an antigen-binding fragment thereof, wherein the antibody comprises a heavy chain variable region comprising HCDR1-HCDR3 with amino acid sequences set forth in SEQ ID NO: 17-SEQ ID NO: 19, respectively; and the antibody comprises a light chain variable region comprising LCDR1-LCDR3 with amino acid sequences set forth in SEQ ID NO: 20-SEQ ID NO: 22, respectively.

Preferably, the IL-1β is human IL-1β.

The variable regions of the light chain and the heavy chain determine the binding of the antigen; the variable region of each chain contains three hypervariable regions, namely complementarity determining regions (CDRs) (the CDRs of the heavy chain (H) include HCDR1, HCDR2, HCDR3, and the CDRs of the light chain (L) include LCDR1, LCDR2, LCDR3; defined by Kabat et al., see Sequences of Proteins of Immunological Interest, Fifth Edition (1991), Volumes 1-3, NIH Publication 91-3242, Bethesda Md).

The antibodies 3H6, 3H6H1L1, 3H6H2L2, 3H6H3L3, and 3H6H4L1 disclosed herein have the same HCDR1-3 and LCDR1-3, according to analysis by technical means well known to those skilled in the art, for example by a VBASE2 database.

The amino acid sequences of the three HCDR regions of the heavy chain variable region are as follows:

```
HCDR 1:
                              (SEQ ID NO: 17)
GFSLSTSGMG,

HCDR 2:
                              (SEQ ID NO: 18)
IYWDDDK,

HCDR 3:
                              (SEQ ID NO: 19)
ARSAYYSFAY;
``` and the amino acid sequences of the three CDR regions of the light chain variable region are as follows:

```
LCDR 1:
                              (SEQ ID NO: 20)
QDVDTD,

LCDR 2:
                              (SEQ ID NO: 21)
WAS,

LCDR 3:
                              (SEQ ID NO: 22)
QQYSSYPT.
```

In one or more embodiments of the present invention, the antibody or the antigen-binding fragment thereof is provided, wherein the heavy chain variable region of the antibody comprises an amino acid sequence selected from SEQ ID NO: 2, SEQ ID NO: 6, SEQ ID NO: 10, and SEQ ID NO: 14; and the light chain variable region of the antibody comprises an amino acid sequence selected from SEQ ID NO: 4, SEQ ID NO: 8, SEQ ID NO: 12, and SEQ ID NO: 16.

In some embodiments of the present invention, the antibody or the antigen-binding fragment thereof is provided, wherein the antibody is selected from:
(1) VH set forth in SEQ ID NO: 2 and VL set forth in SEQ ID NO: 4;
(2) VH set forth in SEQ ID NO: 6 and VL set forth in SEQ ID NO: 8;
(3) VH set forth in SEQ ID NO: 10 and VL set forth in SEQ ID NO: 12; and
(4) VH set forth in SEQ ID NO: 14 and VL set forth in SEQ ID NO: 16.

In one or more embodiments of the present invention, the antibody or the antigen-binding fragment thereof is provided, wherein the antibody or the antigen-binding fragment thereof is selected from Fab, Fab', F(ab')$_2$, Fd, Fv, dAb, a complementarity determining region fragment, a single chain antibody (e.g., scFv), a humanized antibody, a chimeric antibody, and a diabody.

In one or more embodiments of the present invention, the antibody or the antigen-binding fragment thereof is provided, wherein the antibody binds to IL-1β protein with a $K_D$ less than $10^{-5}$ M, such as less than $10^{-6}$ M, less than $10^{-7}$ M, less than $10^{-8}$ M, less than $10^{-9}$ M, or less than $10^{-10}$ M or less; preferably, the $K_D$ is measured by a Biacore molecular interaction instrument.

In some embodiments of the present invention, the antibody or the antigen-binding fragment thereof is provided, wherein the antibody binds to IL-1β protein with an $EC_{50}$ less than about 100 nM, such as less than about 10 nM, less than about 1 nM, less than about 0.9 nM, less than about 0.8 nM, less than about 0.7 nM, less than about 0.6 nM, less than about 0.5 nM, less than about 0.4 nM, less than about 0.3 nM, less than about 0.2 nM, less than about 0.1 nM or less. Specifically, the $EC_{50}$ is measured by an indirect ELISA method.

In one or more embodiments of the present invention, the antibody or the antigen-binding fragment thereof is provided, wherein the antibody comprises a non-CDR region derived from a species other than murine, such as from a human antibody.

In some embodiments of the present invention, the constant regions of the antibodies are humanized, e.g., the heavy chain constant regions are Ig gamma-1 chain C region such as ACCESSION: P01857 or Ig gamma-4 chain C region such as ACCESSION: P01861.1; and the light chain constant regions are Ig kappa chain C region such as ACCESSION: P01834.

In one or more embodiments of the present invention, the antibody or the antigen-binding fragment thereof is provided, wherein the antibody is a monoclonal antibody produced by a hybridoma cell line LT010 deposited at China Center for Type Culture Collection (CCTCC) with an accession number of CCTCC NO: C2018133.

In one or more embodiments of the present invention, the antibody is a monoclonal antibody.

Another aspect of the present invention relates to an antibody-drug conjugate (ADC) comprising an antibody or an antigen-binding fragment thereof and a small molecule drug, wherein the antibody or the antigen-binding fragment thereof is any one of the antibodies or the antigen-binding fragments thereof disclosed herein; preferably, the small molecule drug is a small molecule cytotoxic drug; and more preferably, the small molecule drug is a chemotherapeutic drug.

The chemotherapeutic drug may be a conventional tumor chemotherapeutic drug, such as an alkylating agent, an antimetabolite, an anti-tumor antibiotic, a plant-based anticancer agent, a hormone, and an immunological agent.

In one or more embodiments of the present invention, the antibody-drug conjugate is provided, wherein the antibody or the antigen-binding fragment thereof is linked to a small molecule drug via a linker; the linker may be one known to those skilled in the art, for example, a hydrazone bond, a disulfide bond, or a peptide bond.

In one or more embodiments of the present invention, the antibody-drug conjugate is provided, wherein the molar ratio of the antibody or the antigen-binding fragment thereof to the small molecule drug is 1:1-1:4, for example, 1:1, 1:2, 1:3, or 1:4.

Yet another aspect of the present invention relates to a bispecific antibody (also known as bifunctional antibody) comprising a first protein functional region and a second protein functional region, wherein:
the first protein functional region targets IL-1β, the second protein functional region targets a target other than IL-1β, e.g., IL-17A;
wherein the first protein functional region is any one of the antibodies or the antigen-binding fragments thereof disclosed herein;
preferably, the bispecific antibody is in an IgG-scFv form;
preferably,
(1) the first protein functional region is any one of the antibodies or the antigen-binding fragments thereof disclosed herein, and the second protein functional region is a single chain antibody;
or,
(2) the first protein functional region is a single chain antibody, the heavy chain variable region thereof comprises HCDR1-HCDR3 with amino acid sequences set forth in SEQ ID NO: 17-SEQ ID NO: 19, and the light chain variable region thereof comprises LCDR1-LCDR3 with amino acid sequences set forth in SEQ ID NO: 20-SEQ ID NO: 22, and the second protein functional region is an antibody (e.g., a monoclonal antibody).

In some embodiments of the present invention, the bispecific antibody is provided, wherein the first protein functional region and the second protein functional region are linked directly or via a linker fragment;
preferably, the linker fragment is (GGGGS) m (SEQ ID NO: 23), m being a positive integer such as 1, 2, 3, 4, 5, or 6; or
preferably, the linker fragment is SS (GGGGS) n (SEQ ID NO: 24), n being a positive integer such as 1, 2, 3, 4, 5, or 6.

In some embodiments of the present invention, the bispecific antibody is provided, wherein in item (2),
the heavy chain variable region of the single chain antibody comprises an amino acid sequence selected from SEQ ID NO: 2, SEQ ID NO: 6, SEQ ID NO: 10, and SEQ ID NO: 14; and
the light chain variable region of the single chain antibody comprises an amino acid sequence selected from SEQ ID NO: 4, SEQ ID NO: 8, SEQ ID NO: 12, and SEQ ID NO: 16.

In some embodiments of the present invention, the bispecific antibody is provided, wherein in item (2),
the heavy chain variable region of the single chain antibody comprises an amino acid sequence set forth in SEQ ID NO: 2, and the light chain variable region of the single chain antibody comprises an amino acid sequence set forth in SEQ ID NO: 4;
the heavy chain variable region of the single chain antibody comprises an amino acid sequence set forth in SEQ ID NO: 6, and the light chain variable region of the single chain antibody comprises an amino acid sequence set forth in SEQ ID NO: 8;
the heavy chain variable region of the single chain antibody comprises an amino acid sequence set forth in SEQ ID NO: 10, and the light chain variable region of the single chain antibody comprises an amino acid sequence set forth in SEQ ID NO: 12; or
the heavy chain variable region of the single chain antibody comprises an amino acid sequence set forth in SEQ ID NO: 14, and the light chain variable region of the single chain antibody comprises an amino acid sequence set forth in SEQ ID NO: 16.

In some embodiments of the present invention, the bispecific antibody is provided, wherein the numbers of the first protein functional region and the second protein functional region are each independently 1, 2 or more.

In some embodiments of the present invention, the bispecific antibody is provided, wherein in item (2), the constant region of the monoclonal antibody is selected from constant regions of human IgG1, IgG2, IgG3, and IgG4.

In some embodiments of the present invention, the bispecific antibody is provided, wherein the single chain antibody is linked to the C-terminus of the heavy chain of the antibody or the monoclonal antibody.

Yet another aspect of the present invention relates to an isolated nucleic acid molecule comprising a nucleotide sequence encoding an antibody heavy chain variable region and a nucleotide sequence encoding an antibody light chain variable region, wherein
the antibody heavy chain variable region comprises HCDR1-HCDR3 with amino acid sequences set forth in SEQ ID NO: 17-SEQ ID NO: 19, respectively, and the antibody light chain variable region comprises LCDR1-LCDR3 with amino acid sequences set forth in SEQ ID NO: 20-SEQ ID NO: 22, respectively;
preferably, the amino acid sequence of the antibody heavy chain variable region is selected from SEQ ID NO: 2, SEQ ID NO: 6, SEQ ID NO: 10, and SEQ ID NO: 14, and the amino acid sequence of the antibody light chain variable region is selected from SEQ ID NO: 4, SEQ ID NO: 8, SEQ ID NO: 12, and SEQ ID NO: 16;
more preferably, the amino acid sequence of the antibody heavy chain variable region is set forth in SEQ ID NO: 2, and the amino acid sequence of the antibody light chain variable region is set forth in SEQ ID NO: 4; the amino acid sequence of the antibody heavy chain variable region is set forth in SEQ ID NO: 6, and the amino acid sequence of the antibody light chain variable region is set forth in SEQ ID NO: 8; the amino acid sequence of the antibody heavy chain variable region is set forth in SEQ ID NO: 10, and the amino acid sequence of the antibody light chain variable region is set forth in SEQ ID NO: 12; or the amino acid sequence of the antibody heavy chain variable region is set forth in SEQ ID NO: 14, and the amino acid sequence of the antibody light chain variable region is set forth in SEQ ID NO: 16; and
even more preferably, the isolated nucleic acid molecule comprises:
nucleotide sequences set forth in SEQ ID NO: 1 and SEQ ID NO: 3,
nucleotide sequences set forth in SEQ ID NO: 5 and SEQ ID NO: 7,
nucleotide sequences set forth in SEQ ID NO: 9 and SEQ ID NO: 11, or
nucleotide sequences set forth in SEQ ID NO: 13 and SEQ ID NO: 15.

The isolated nucleic acid molecule may be a single nucleic acid molecule or multiple nucleic acid molecules, such as two nucleic acid molecules. In the case of a single nucleic acid molecule, the heavy chain variable region and the light chain variable region of the antibody may be expressed by the same nucleic acid molecule, e.g., by the same or different expression cassettes located on the same nucleic acid molecule. In the case of multiple nucleic acid molecules, for example, two nucleic acid molecules, the heavy chain variable region and the light chain variable region of the antibody may be expressed by different nucleic acid molecules.

Yet another aspect of the present invention relates to a recombinant vector comprising the isolated nucleic acid molecule disclosed herein. The number of the recombinant vector may be one or more. In the case of multiple (e.g., two) nucleic acid molecules, the multiple (e.g., two) nucleic acid molecules may be expressed by the same recombinant vector or by different recombinant vectors.

Yet another aspect of the present invention relates to a host cell comprising the isolated nucleic acid molecule or the recombinant vector disclosed herein.

Yet another aspect of the present invention relates to a method for preparing any one of the antibodies or the antigen-binding fragments thereof disclosed herein, comprising cultivating the host cell disclosed herein in a suitable condition, and isolating the antibody or the antigen-binding fragment thereof from the cell cultures.

Yet another aspect of the present invention relates to a hybridoma cell line LT010 deposited at China Center for Type Culture Collection (CCTCC) with an accession number of CCTCC NO: C2018133.

Yet another aspect of the present invention relates to a pharmaceutical composition comprising any one of the antibodies or the antigen-binding fragments thereof disclosed herein, the antibody-drug conjugate disclosed herein, or the bispecific antibody disclosed herein; optionally, the pharmaceutical composition further comprises pharmaceutically acceptable carriers and/or excipients.

Yet another aspect of the present invention relates to use of any one of the antibodies or the antigen-binding fragments thereof disclosed herein, the antibody-drug conjugate disclosed herein, or the bispecific antibody disclosed herein in preparing a medicament for the treatment and/or prevention of autoimmune diseases, cardiovascular and cerebrovascular diseases, tumors, cryopyrin-associated periodic syndromes in children and adults, systemic juvenile idiopathic arthritis, or gouty arthritis;
preferably, the autoimmune disease is selected from rheumatoid arthritis, multiple sclerosis, and periodic fever syndromes;
preferably, the periodic fever syndrome is selected from TNF receptor-associated periodic syndrome (TRAPS), hyper-IgD syndrome (HIDS)/mevalonate kinase deficiency (MKD), and familial mediterranean fever (FMF);
preferably, the cryopyrin-associated periodic syndrome in children and adults is selected from familial cold autoinflammatory syndrome, Muckle-Wells syndrome, neonatal-onset multisystem inflammatory disease, chronic infantile neurological cutaneous and articular syndrome, and familial cold urticaria;

preferably, the cardiovascular and cerebrovascular disease is selected from myocardial infarction, atherosclerosis, arterial thrombosis, and cerebralvascular accident;

preferably, the tumor is selected from lung cancer, hepatocellular carcinoma, and acute myeloid leukemia; and preferably, the gouty arthritis is acute gouty arthritis or chronic gouty arthritis.

Yet another aspect of the present invention relates to use of any one of the antibodies or the antigen-binding fragments thereof disclosed herein, the antibody-drug conjugate disclosed herein, or the bispecific antibody disclosed herein in preparing:

a medicament for blocking the binding of human IL-1β to human IL-1R1 and/or human IL-1R2, a medicament for down-regulating the activity or level of human IL-1β, or a medicament for inhibiting the activation of downstream signaling pathways mediated by the binding of human IL-1β to human IL-1R1 and/or human IL-1R2.

In one embodiment of the present invention, the human IL-1R1 and/or human IL-1R2 is human IL-1R1 and/or human IL-1R2 on the cell surface.

In one embodiment of the present invention, the use is non-therapeutic and/or non-diagnostic.

In one or more embodiments of the present invention, the antibody or the antigen-binding fragment thereof disclosed herein, the antibody-drug conjugate disclosed herein, or the bispecific antibody disclosed herein is for use in the treatment and/or prevention of autoimmune diseases, cardiovascular and cerebrovascular diseases, tumors, cryopyrin-associated periodic syndromes in children and adults, systemic-onset juvenile idiopathic arthritis, or gouty arthritis;

preferably, the autoimmune disease is selected from rheumatoid arthritis, multiple sclerosis, and periodic fever syndromes;

preferably, the periodic fever syndrome is selected from TNF receptor-associated periodic syndrome (TRAPS), hyper-IgD syndrome (HIDS)/mevalonate kinase deficiency (MKD), and familial mediterranean fever (FMF);

preferably, the cryopyrin-associated periodic syndrome in children and adults is selected from familial cold autoinflammatory syndrome, Muckle-Wells syndrome, neonatal-onset multisystem inflammatory disease, chronic infantile neurological cutaneous and articular syndrome, and familial cold urticaria;

preferably, the cardiovascular and cerebrovascular disease is selected from myocardial infarction, atherosclerosis, arterial thrombosis, and cerebralvascular accident;

preferably, the tumor is selected from lung cancer, hepatocellular carcinoma, and acute myeloid leukemia; and preferably, the gouty arthritis is acute gouty arthritis or chronic gouty arthritis.

In one or more embodiments of the present invention, the antibody or the antigen-binding fragment disclosed herein, the antibody-drug conjugate disclosed herein, or the bispecific antibody disclosed herein is for use in:

blocking the binding of human IL-1β to human IL-1R1 and/or human IL-1R2, down-regulating the activity or level of human IL-1β, or inhibiting the activation of downstream signaling pathways mediated by the binding of human IL-1β to human IL-1R1 and/or human IL-1R2.

In one embodiment of the present invention, the human IL-1R1 and/or human IL-1R2 is human IL-1R1 and/or human IL-1R2 on the cell surface.

Yet another aspect of the present invention relates to an in vivo or in vitro method comprising: administering to a cell an effective amount of any one of the antibodies or the antigen-binding fragments thereof disclosed herein, the antibody-drug conjugate disclosed herein, or the bispecific antibody disclosed herein, wherein the method is selected from:

a method for blocking the binding of human IL-1β to human IL-1R1 and/or human IL-1R2, a method for down-regulating the activity or level of human IL-1β, and a method for inhibiting the activation of downstream signaling pathways mediated by the binding of human IL-1β to human IL-1R1 and/or human IL-1R2.

In one embodiment of the present invention, the human IL-1R1 and/or human IL-1R2 is human IL-1R1 and/or human IL-1R2 on the cell surface.

In one embodiment of the present invention, the in vitro method is non-therapeutic and/or non-diagnostic.

Yet another aspect of the present invention relates to a method for treating and/or preventing autoimmune diseases, cardiovascular and cerebrovascular diseases, tumors, cryopyrin-associated periodic syndromes in children and adults, systemic juvenile idiopathic arthritis, or gouty arthritis, comprising: administering to a subject in need an effective amount of any one of the antibodies or the antigen-binding fragments thereof disclosed herein, the antibody-drug conjugate disclosed herein, or the bispecific antibody disclosed herein;

preferably, the autoimmune disease is selected from rheumatoid arthritis, multiple sclerosis, and periodic fever syndromes;

preferably, the periodic fever syndrome is selected from TNF receptor-associated periodic syndrome (TRAPS), hyper-IgD syndrome (HIDS)/mevalonate kinase deficiency (MKD), and familial mediterranean fever (FMF);

preferably, the cryopyrin-associated periodic syndrome in children and adults is selected from familial cold autoinflammatory syndrome, Muckle-Wells syndrome, neonatal-onset multisystem inflammatory disease, chronic infantile neurological cutaneous and articular syndrome, and familial cold urticaria;

preferably, the cardiovascular and cerebrovascular disease is selected from myocardial infarction, atherosclerosis, arterial thrombosis, and cerebralvascular accident;

preferably, the tumor is selected from lung cancer, hepatocellular carcinoma, and acute myeloid leukemia; and preferably, the gouty arthritis is acute gouty arthritis or chronic gouty arthritis.

The inventors found from animal experiments that the antibodies disclosed herein, particularly 3H6H4L1, can effectively alleviate pathological changes in a rheumatoid arthritis model induced by NIH/3T3 cells transfected with human IL-1β in BALB/c mice, characterized in that the administration of the antibody 3H6H4L1 can effectively improve the pathological behaviors and reduce the swelling area of affected limbs of the rheumatoid mice.

In the present invention, unless otherwise defined, the scientific and technical terms used herein have the meanings generally understood by those skilled in the art. In addition, the laboratory operations of cell culture, molecular genetics, nucleic acid chemistry and immunology used in the present invention are the routine operations widely used in the corresponding fields. Meanwhile, in order to better understand the present invention, the definitions and explanations of the relevant terms are provided below.

As used herein, when referring to the amino acid sequence of IL-1β (GenBank ID: NP_000567.1), it includes the full length of the IL-1 protein, as well as a fusion protein of IL-1β, such as a fragment fused to a mouse or human IgG Fc protein fragment (mFc or hFc) or multiple His. However, it is understood by those skilled in the art that in the amino acid sequence of IL-1β, mutations or variations (including but not limited to substitutions, deletions and/or additions) can be naturally generated or artificially introduced without affecting biological functions thereof. Thus, in the present invention, the term "IL-1β" shall include all such sequences as well as natural or artificial variants thereof. In addition, when a sequence fragment of the IL-1β protein is described, it includes the sequence fragment of IL-1β as well as the corresponding sequence fragments in natural or artificial variants thereof.

As used herein, when referring to the amino acid sequence of IL-1R1 (GenBank ID: NP_000868), it includes the full length of the IL-1R1 protein, as well as a fusion protein of IL-1R1, such as a fragment fused to a mouse or human IgG Fc protein fragment (mFc or hFc) or multiple His. However, it is understood by those skilled in the art that in the amino acid sequence of the IL-1R1 protein, mutations or variations (including but not limited to substitutions, deletions and/or additions) can be naturally generated or artificially introduced without affecting biological functions thereof. Thus, in the present invention, the term "IL-1R1" shall include all such sequences as well as natural or artificial variants thereof. In addition, when a sequence fragment of the IL-1R1 protein is described, it includes the sequence fragment of IL-1R1 as well as the corresponding sequence fragments in natural or artificial variants thereof.

As used herein, when referring to the amino acid sequence of IL-1R2 (GenBank ID: CAA42441.1), it includes the full length of the IL-1R2 protein, as well as a fusion protein of IL-1R2, such as a fragment fused to a mouse or human IgG Fc protein fragment (mFc or hFc) or multiple His. However, it is understood by those skilled in the art that in the amino acid sequence of the IL-1R2 protein, mutations or variations (including but not limited to substitutions, deletions and/or additions) can be naturally generated or artificially introduced without affecting biological functions thereof. Thus, in the present invention, the term "IL-1R2" shall include all such sequences as well as natural or artificial variants thereof. In addition, when a sequence fragment of the IL-1R2 protein is described, it includes the sequence fragment of IL-1R2 as well as the corresponding sequence fragments in natural or artificial variants thereof.

As used herein, the term "$EC_{50}$" refers to the concentration for 50% of maximal effect, i.e. the concentration that can cause 50% of the maximal effect.

As used herein, the term "antibody" refers to an immunoglobulin molecule that generally consists of two pairs of polypeptide chains (each pair with one "light" (L) chain and one "heavy" (H) chain). Antibody light chains are classified as k and λ light chains. Heavy chains are classified as u, δ, γ, a, or s. And isotypes of antibodies are defined as IgM, IgD, IgG, IgA, and IgE. In light chains and heavy chains, the variable region and constant region are linked by a "J" region of about 12 or more amino acids, and the heavy chain also comprises a "D" region of about 3 or more amino acids. Each heavy chain consists of a heavy chain variable region (VH) and a heavy chain constant region (CH). The heavy chain constant region consists of 3 domains (CH1, CH2, and CH3). Each light chain consists of a light chain variable region (VL) and a light chain constant region (CL). The light chain constant region consists of one domain CL. The constant region of the antibody can mediate the binding of immunoglobulins to host tissues or factors, including the binding of various cells of the immune system (e.g., effector cells) to the first component (Clq) of the classical complement system. The VH and VL regions can be further subdivided into hypervariable regions (called complementarity determining regions or CDRs), between which conservative regions called framework regions (FRs) are distributed. Each VH and VL consists of 3 CDRs and 4 FRs arranged from amino terminus to carboxyl terminus in the following order: FR1, CDR1, FR2, CDR2, FR3, CDR3, FR4. The variable regions (VH and VL) of each heavy chain/light chain pair form an antibody-binding site, respectively. The assignment of amino acids to each region or domain follows the definition of Kabat Sequences of Proteins of Immunological Interest (National Institutes of Health, Bethesda, Md. (1987 and 1991)), Chothia & Lesk (1987) *J. Mol. Biol.* 196:901-917, or Chothia et al. (1989) *Nature* 342:878-883. The term "antibody" is not restricted by any specific method for producing antibody. For example, the antibody includes, in particular, a recombinant antibody, a monoclonal antibody, and a polyclonal antibody. The antibodies can be different isotypes, e.g., antibodies IgG (e.g., subtypes IgG1, IgG2, IgG3, or IgG4), IgA1, IgA2, IgD, IgE, or IgM.

As used herein, the term "antigen-binding fragment", also known as the "antigen-binding moiety", refers to the polypeptide comprising the fragment of a full-length antibody, which maintains the ability to specifically bind to an antigen which is the same as the one the full-length antibody binds to, and/or competes with the full-length antibody for the specific binding to an antigen. See generally, Fundamental Immunology, Ch. 7 (Paul, W., ed., 2nd edition, Raven Press, N.Y. (1989), which is incorporated by reference herein in its entirety for all purposes. Antigen-binding fragment of the antibody can be produced by recombinant DNA technique or by enzymatic or chemical cleavage of intact antibodies. In some cases, the antigen-binding fragment include Fab, Fab', F(ab')$_2$, Fd, Fv, dAb, and a complementarity determining region (CDR) fragment, a single chain antibody (e.g., scFv), a chimeric antibody, a diabody, and a polypeptide that comprise at least a portion of the antibody sufficient to confer specific antigen-binding ability on the polypeptide.

In some cases, the antigen-binding fragment of the antibody is a single chain antibody (e.g., scFv), in which the VL and VH domains are paired to form a monovalent molecule via a linker that enables them to produce a single polypeptide chain (see, e.g., Bird et al., *Science* 242:423 426 (1988) and Huston et al., *Proc. Natl. Acad. Sci. USA* 85:5879 5883 (1988)). Such scFv molecules may have a general structure: NH2-VL-linker-VH—COOH or NH2-VH-linker-VL-COOH. An appropriate prior art linker consists of a repeating GGGGS (SEQ ID NO: 25) amino acid sequence or a variant thereof. For example, a linker having the amino acid sequence (GGGGS) 4 (SEQ ID NO: 26) can be used, but a variant thereof can also be used (Holliger et al. (1993), *Proc. Natl. Acad. Sci. USA* 90:6444-6448). Other linkers that can be used in the present invention are described by Alfthan et al. (1995), *Protein Eng.* 8:725-731, Choi et al. (2001), *Eur. J. Immunol.* 31:94-106, Hu et al. (1996), *Cancer Res.* 56:3055-3061, Kipriyanov et al. (1999), *J. Mol. Biol.* 293: 41-56 and Roovers et al. (2001), *Cancer Immunol.*

In some cases, the antigen-binding fragment of the antibody is a diabody, that is, a bivalent antibody, in which the VH and VL domains are expressed on a single polypeptide chain. However, the linker used is too short to allow the pairing of the two domains on the same chain, thereby the domains are forced to pair with the complementary domains on the other chain and two antigen binding sites are generated (see, e.g., Holliger P. et al., *Proc. Natl. Acad. Sci. USA* 90:6444-6448 (1993), and Poljak R J et al., *Structure* 2:1121-1123 (1994)).

In other cases, the antigen-binding fragment of the antibody is a "bifunctional antibody". The bifunctional antibody, also known as bispecific antibody, is a specific drug that targets two different antigens simultaneously, and can be produced by immunoselection purification. In addition, the bispecific antibody can also be produced by genetic engineering, which has certain advantages due to corresponding flexibility in aspects such as the optimization of binding sites, consideration of synthetic form, and yield. Currently, the bispecific antibody has been demonstrated to exist in over 45 forms (Müller D, Kontermann R E. Bispecific antibodies for cancer immunotherapy: Current perspectives. *BioDrugs* 2010; 24:89-98). A number of bispecific antibodies have been developed in the form of IgG-ScFv, namely the Morrison form (1997 Coloma M J, Morrison S L. Design and production of novel tetravalent bispecific antibodies. *Nature Biotechnology*, 1997; 15:159-163), which has been demonstrated to be one of the ideal forms of the bispecific antibodies because of its similarity to the naturally existing IgG form and advantages in antibody engineering, expression and purification (Miller B R, Demarest S J, et al., Stability engineering of scFvs for the development of bispecific and multivalent antibodies. *Protein Eng Des Sel* 2010; 23:549-57; Fitzgerald J, Lugovskoy A. Rational engineering of antibody therapeutics targeting multiple oncogene pathways. *MAbs* 2011; 3:299-309).

Antigen-binding fragments of antibodies (e.g., the antibody fragments described above) can be obtained from a given antibody (e.g., monoclonal antibody 3H6, 3H6H1L1, 3H6H2L2, 3H6H3L3, or 3H6H4L1 provided herein) using conventional techniques known to those skilled in the art (e.g., recombinant DNA technique or enzymatic or chemical cleavage), and the antigen-binding fragments of antibodies are screened for specificity in the same manner as for intact antibodies.

As used herein, the terms "mAb" and "monoclonal antibody" refer to an antibody or a fragment of an antibody that is derived from a group of highly homologous antibodies, i.e. from a group of identical antibody molecules, except for natural mutations that may occur spontaneously. The monoclonal antibody has a high specificity for a single epitope on an antigen. The polyclonal antibody, relative to the monoclonal antibody, generally comprises at least two or more different antibodies which generally recognize different epitopes on an antigen. Monoclonal antibodies can generally be obtained using hybridoma technique first reported by Kohler et al. (*Nature*, 256:495, 1975), but can also be obtained using recombinant DNA technique (see, e.g., U.S. Pat. No. 4,816,567).

As used herein, the term "humanized antibody" refers to an antibody or an antibody fragment obtained when all or a part of CDR regions of a human immunoglobulin (receptor antibody) are replaced by the CDR regions of a non-human antibody (donor antibody), wherein the donor antibody may be a non-human (e.g., mouse, rat or rabbit) antibody having expected specificity, affinity, or reactivity. In addition, some amino acid residues in the framework regions (FRs) of the receptor antibody can also be replaced by the amino acid residues of corresponding non-human antibodies or by the amino acid residues of other antibodies to further improve or optimize the performance of the antibody. For more details on humanized antibodies, see, for example, Jones et al., *Nature*, 321:522 525 (1986); Reichmann et al., *Nature*, 332:323 329 (1988); Presta, *Curr. Op. Struct. Biol.*, 2:593 596 (1992); and Clark, *Immunol. Today* 21:397 402 (2000).

As used herein, the term "isolated" refers to obtained by artificial means from natural state. If a certain "isolated" substance or component appears in nature, it may be due to the change in its natural environment, or it is isolated from the natural environment, or both. For example, a certain non-isolated polynucleotide or polypeptide naturally exists in a certain living animal, and the same polynucleotide or polypeptide with a high purity isolated from such a natural state is called isolated polynucleotide or polypeptide. The term "isolated" does not exclude the existence of artificial or synthetic substances or other impurities that do not affect the activity of the substance.

As used herein, the term "vector" refers to a nucleic acid vehicle into which a polynucleotide can be inserted. When the vector allows for the expression of the protein encoded by the inserted polynucleotide, the vector is called an expression vector. A vector can be introduced into a host cell by transformation, transduction, or transfection so that the genetic substance elements carried by the vector can be expressed in the host cell. Vectors are well known to those skilled in the art, including but not limited to: plasmids; phagemids; cosmids; artificial chromosomes, such as yeast artificial chromosomes (YAC), bacterial artificial chromosomes (BAC), or P1-derived artificial chromosomes (PAC); phages such as lambda phages or M13 phages, and animal viruses. Animal viruses that can be used as vectors include, but are not limited to, retroviruses (including lentiviruses), adenoviruses, adeno-associated viruses, herpes viruses (such as herpes simplex virus), poxviruses, baculoviruses, papillomaviruses, and papovaviruses (such as SV40). A vector can contain a variety of elements that control expression, including, but not limited to, promoter sequences, transcription initiation sequences, enhancer sequences, selection elements, and reporter genes. In addition, the vector may further contain a replication initiation site.

As used herein, the term "host cell" refers to cells that can be used to introduce vectors, including but not limited to, prokaryotic cells such as *E. coli* or *B. subtilis*, fungal cells such as yeast cells or *aspergillus*, insect cells such as S2 *drosophila* cells or Sf9, or animal cells such as fibroblast, CHO cells, COS cells, NSO cells, HeLa cells, BHK cells, HEK 293 cells, or human cells.

As used herein, the term "bispecific", "dual-specificity" or "bifunctional" antigen-binding protein or antibody is a hybrid antigen-binding protein or antibody having two different antigen-binding sites, respectively. A bispecific antibody is a multispecific antigen-binding protein or multispecific antibody, and can be produced by a variety of methods, including but not limited to, fusion of hybridomas or linkage of Fab' fragments. See, e.g., Songsivilai and Lachmann, 1990, *Clin. Exp. Immunol.* 79:315-321; Kostelny et al. 1992, *J. Immunol.* 148:1547-1553. The two binding sites of a bispecific antigen-binding protein or antibody will bind two different epitopes that are present in the same or different protein targets.

As used herein, the term "specifically bind" refers to a non-random binding reaction between two molecules, such as a reaction between an antibody and an antigen it targets. In some embodiments, an antibody that specifically binds to an antigen (or an antibody that is specific for an antigen) means that the antibody binds to the antigen with an affinity ($K_D$) of less than about $10^{-5}$ M, such as less than about $10^{-6}$ M, less than about $10^{-7}$ M, less than about $10^{-8}$ M, less than about $10^{-9}$ M, or less than about $10^{-10}$ M or less.

As used herein, the term "$K_D$" refers to a dissociation equilibrium constant for a specific antibody-antigen interaction, which is used to describe the binding affinity between the antibody and the antigen. The smaller the equilibrium dissociation constant, the tighter the antibody-antigen binding, and the higher the affinity between the antibody and the antigen. Typically, an antibody (e.g., monoclonal antibody 3H6, 3H6H1L1, 3H6H2L2, or 3H6H3L3 disclosed herein) binds to an antigen (e.g., IL-1β protein) with a dissociation equilibrium constant ($K_D$) of less than about $10^{-5}$ M, such as less than about $10^{-6}$ M, less than about $10^{-7}$ M, less than about $10^{-8}$ M, less than about $10^{-9}$ M, or less than about $10^{-10}$ M or less. $K_D$ can be determined using methods known to those skilled in the art, for example using a Biacore molecular interaction instrument.

As used herein, the terms "monoclonal antibody" and "mAb" have the same meaning and can be used interchangeably; the terms "polyclonal antibody" and "PcAb" have the same meaning and can be used interchangeably; the terms "polypeptide" and "protein" have the same meaning and can be used interchangeably. And in the present invention, amino acids are generally represented by single-letter and three-letter abbreviations known in the art. For example, alanine can be represented by A or Ala.

As used herein, the terms "hybridoma" and "hybridoma cell line" can be used interchangeably, and when referring to the terms "hybridoma" and "hybridoma cell line", they also include subclones and progeny cells of the hybridoma. For example, when referring to the hybridoma cell line LT010, it also refers to subclones and progeny cells of the hybridoma cell line LT010.

As used herein, the term "pharmaceutically acceptable carrier and/or excipient" refers to a carrier and/or excipient that is pharmacologically and/or physiologically compatible with the subject and the active ingredient, which is well known in the art (see, e.g., Remington's Pharmaceutical Sciences. Edited by Gennaro A R, 19th ed. Pennsylvania: Mack Publishing Company, 1995) and includes but is not limited to pH regulators, surfactants, adjuvants, and ionic strength enhancers. For example, the pH regulators include, but are not limited to, phosphate buffer; the surfactants include, but are not limited to, cationic, anionic, or non-ionic surfactants, such as Tween-80; and the ionic strength enhancers include, but are not limited to, sodium chloride.

As used herein, the term "effective amount" refers to an amount sufficient to obtain or at least partially obtain desired effect. For example, a prophylactically (e.g., RA) effective amount refers to an amount sufficient to prevent, stop, or delay the onset of diseases (e.g., RA); a therapeutically effective amount refers to an amount sufficient to cure or at least partially stop a disease and complications thereof in patients suffering from the disease. It is well within the ability of those skilled in the art to determine such an effective amount. For example, the amount effective for therapeutic use will depend on the severity of the disease to be treated, the overall state of the patient's own immune system, the general condition of the patient such as age, weight and gender, the manner of drug administration, and other treatments administered concurrently, etc.

Advantages of the Invention

The anti-IL-1β antibody disclosed herein, in particular the humanized anti-IL-1β antibody, has one or more of the following technical effects:

(1) effectively binding to human IL-1β and blocking the binding of IL-1β to a receptor IL-1R1 thereof;
(2) inhibiting the activation of a downstream signaling pathway of IL-1β;
(3) having the ability of specifically inhibiting the activity of IL-1β for inducing MRC-5 cells to secrete IL-6;
(4) having the ability of effectively blocking the activation of IL-1β on NF-κB;
(5) having the potential of being used in preparing a medicament for inhibiting IL-1β; and
(6) having the potential of being used in preparing a medicament for preventing and/or treating diseases such as rheumatoid arthritis, gout, multiple sclerosis, cardiovascular events and/or cardiovascular diseases, tumors, cryopyrin-associated periodic syndromes in children and adults, periodic fever syndromes, systemic juvenile idiopathic arthritis.

DETAILED DESCRIPTION

Figure 1:
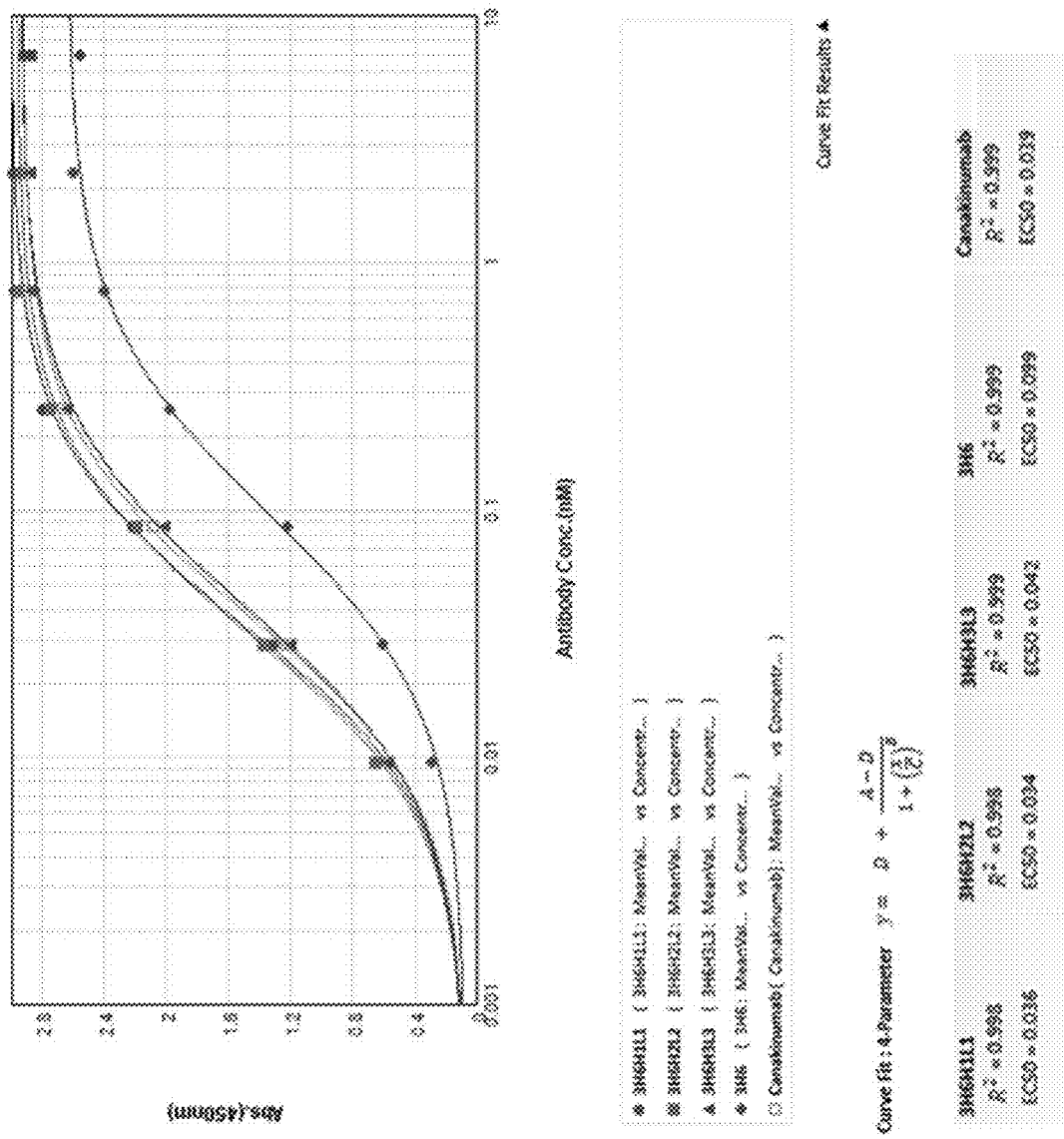
FIG. 1. Assay results of the binding activity of 3H6, 3H6H1L1, 3H6H2L2, and 3H6H3L3 to human IL-1β-His-Bio.

The embodiments of the present invention will be described in detail below with reference to the examples. Those skilled in the art will understand that the following examples are only used to illustrate the present invention, and should not be regarded as limiting the scope of the present invention. The cases without the specific descriptions of techniques or conditions were carried out according to the technologies or conditions described in the literature in the art (e.g., see, *Guide to Molecular Cloning Experiments*, authored by J. Sambrook et al., and translated by Huang Peitang et al., third edition, Science Press) or according to the product manual. Reagents or instruments used are commercially available conventional products if the manufacturers thereof are not specified.

In the following examples of the present invention, BALB/c mice used were purchased from Guangdong Medical Experimental Animal Center.

In the following examples of the present invention, the marketed antibody canakinumab for the same target (trade name Ilaris®) was purchased from Novartis used as a control antibody.

Preparation Example 1. Preparation of Fusion Proteins Human IL-1β-his, IL-1R1 (1-332)-his, IL-1β-hFc, and Human IL-1β-his-Bio The protein sequences of human IL-1β (Genbank ID: NP_000567.1) and IL-1R1 (Genbank ID: NP_000868) were found from NCBI GenBank protein database. The amino acid sequences of human IL-1β and IL-1R1 were fused to the sequences of His tag and human IgG Fc purification tag respectively, with names abbreviated as human IL-1β-His, IL-1R1 (1-332)-His, IL-1β-hFc respectively.

The quality of the protein samples was qualified by SDS-PAGE.

The biotinylated human IL-1β-His protein samples (referred to as human IL-1β-His-Bio for short) were prepared by using EZ-Link® Sulfo-NHS-LC-Biotinylation Kit (Thermo scientific), and the specific preparation method was performed by referring to the kit manual.

The prepared fusion proteins were used in the following examples.

Example 1. Preparation of Anti-IL-1β Murine Antibody 3H6

1. Preparation of the Hybridoma Cell Line LT010

BALB/c mice (purchased from Guangdong Medical Laboratory Animal Center) were immunized by human IL-1β-his as an antigen, and spleen cells of the immunized mice were fused to mouse myeloma cells to form hybridoma cells. The hybridoma cells were screened using IL-1β-His-Bio as an antigen by ELISA to give the hybridoma cells capable of secreting the antibody specifically binding to the IL-1β-His-Bio. The resulting hybridoma cells by ELISA were screened by competitive ELISA to give the hybridoma cells capable of secreting the antibody which competes with the receptor IL-1R1 (1-332)-His for binding to IL-1β-hFc, and a stable hybridoma cell line was obtained by limiting dilution. For methods for hybridoma cell preparation, referring to currently established methods (e.g., Stewart, S. J., "Monoclonal Antibody Production", in Basic Methods in antibody Production and Characterization, Eds. G. C. Howard and D. R. Bethell, Boca Raton: CRC Press, 2000).

The inventors named the above hybridoma cell line as the hybridoma cell line LT010 (IL-1β-3H6), and named the monoclonal antibody secreted by it as 3H6.

Hybridoma cell line LT010 (IL-1β-3H6) was deposited at China Center for Type Culture Collection (CCTCC) on Jun. 21, 2018 with an accession number of CCTCC NO: C2018133, and a preservation address of Wuhan University, Wuhan, China, postal code: 430072.

2. Preparation of Anti-IL-1β Antibody 3H6

The LT010 cell line prepared above was cultured in the hybridoma-containing serum-free medium (hybridoma serum-free medium containing 1% penicillin-streptomycin and 4% Glutamax, cultured in a cell incubator at 37° C. with 5% CO2). After 7 days, the cell culture supernatant was collected, and subjected to high-speed centrifugation, vacuum filtration through a microfiltration membrane, and purification through a HiTrap protein A HP column to give antibody 3H6. And the purified 3H6 sample was qualified by SDS-PAGE electrophoresis.

Example 2. Sequence Analysis on Anti-IL-1β Antibody 3H6 mRNA was extracted from the LT010 cell line cultured in Example 1 according to the method of the cultured cell bacterial total RNA extraction kit (Tiangen, Cat no. DP430). cDNA was synthesized according to the kit manual of Invitrogen SuperScript III First-Strand Synthesis System for RT-PCR and amplified by PCR. The PCR-amplified products were directly TA cloned, and the kit manual of the pEASY-T1 Cloning Kit (Transgen CT101) was referred to for specific operations.

The TA-cloned products were directly sequenced, and the sequencing results are as follows:

The nucleotide sequence encoding the heavy chain variable region of antibody 3H6:

(354 bp)

(SEQ ID NO: 1)
CAGGTGACCCTGAAGGAGAGCGGACCAGGAATCCTGCAGCCTAGCCAGAC

ACTGAGCCTGACTTGCAGCTTCAGCGGCTTCAGCCTGAGCACAAGCGGAA

TGGGCGTGTCTTGGATCAGGCAGCCATCAGGAAAGGGACTCGAGTGGCTG

GCTCACATCTACTGGGACGACGACAAGCGGTACAACCCCTCCCTGAAGAG

CAGGCTGACCATCAGCAAGGACACCAGCAGCAACCAGGTGTTCCTGAAGA

TCACCAGCGTGGACACCGCCGATAGCGCTACCTACTATTGCGCCAGAAGC

GCCTACTACAGCTTCGCCTATTGGGGCCAGGGAACACTGGTGTCCGTGTC

AGCC

The amino acid sequence of the heavy chain variable region of antibody 3H6 is as follows: (118 aa, in which the underlined amino acid sequences are CDR regions)

(SEQ ID NO: 2)
QVTLKESGPGILQPSQTLSLTCSFSGFSLSTSGMGVSWIRQPSGKG

LEWLAHIYWDDDKRYNPSLKSRLTISKDTSSNQVFLKITSVDTADS

ATYYCARSAYYSFAYWGQGTLVSVSA

The nucleotide sequence encoding the light chain variable region of antibody 3H6:

(318 bp)

(SEQ ID NO: 3)
GATATCGTCATGACACAGTCACATAAGTTTATGTCTACTAGTG

TGGGCGGGCGGGTCAGAATTACCTGTAAGGCCTCTCAGGACGT

GGATACAGACGTGGCTTGGTTCCAGCAGAAGCCCGGACAGAGC

CCTAAACTGCTGATCTACTGGGCCTCCACAAGGCACACTGGGG

TGCCAGATCGGTTCACTGGATCAGGCAGCGGGACCGACTTTAC

TCTGACCATTTCCAACGTCCAGTCTGAGGATCTGGCTGACTAT

TTCTGCCAGCAGTACAGCTCCTATCCCACCTTTGGAGCAGGCA

CAAAGCTGGAACTGAAA

The amino acid sequence of the light chain variable region of antibody 3H6 is as follows: (106 aa, in which the underlined amino acid sequences are CDR regions)

(SEQ ID NO: 4)
DIVMTQSHKFMSTSVGGRVRITCKAS<u>QDVDTDVA</u>WFQQ

KPGQSPKW<u>YWAS</u>TRHTGVPDRFTGSGSGTDFTLTISNV

QSEDLADYFC<u>QQYSSYPT</u>FGAGTKLELK

Example 3. Design and Preparation of Anti-IL-1β Humanized Antibodies 3H6H1L1, 3H6H2L2, 3H6H3L3, and 3H6H4L1

1. Design of the Light and Heavy Chain Sequences of Anti-IL-1β Humanized Antibodies 3H6H1L1, 3H6H2L2, 3H6H3L3, and 3H6H4L1

Based on the three-dimensional crystal structure of IL-1β protein (van Oostrum J, Priestle J P, Grütter MG, Schmitz A. The structure of murine interleukin-1 beta at 2.8 A resolution. *J Struct Biol.* 1991, 107 (2): 189-95.) and the sequence obtained in Example 2, sequences of the heavy and light chain variable regions of the humanized antibodies 3H6H1L1, 3H6H2L2, 3H6H3L3, and 3H6H4L1 were designed (sequences of the constant regions of antibodies 3H6H1L1, 3H6H2L2, and 3H6H3L3 are from the NCBI database, in which the heavy chain constant region is Ig gamma-1 chain C region, ACCESSION: P01857, and the constant region is Ig kappa chain C region, ACCESSION: P01834; sequences of the constant regions of antibody 3H6H4L1 are from the NCBI database, in which the heavy chain constant region is Ig gamma-4 chain C region, ACCESSION: P01861.1, and the light chain constant region is Ig kappa chain C region, ACCESSION: P01834).

The sequences of heavy and light chain variable regions of humanized antibodies 3H6H1L1, 3H6H2L2, 3H6H3L3, and 3H6H4L1 are as follows:

(1) Humanized Monoclonal Antibody 3H6H1L1

The nucleotide sequence encoding the heavy chain variable region of antibody 3H6H1L1:

(354 bp)
(SEQ ID NO: 5)
CAGGTGACACTGAAGGAGTCTGGCCCCGCCCTGCTGAAG

CCTACCCAGACACTGACCCTGACATGTACCTTCTCCGGC

TTTTCTCTGAGCACCTCCGGCATGGGCGTGTCTTGGATC

AGGCAGCCAAGCGGCAAGGCCCTGGAGTGGCTGGCACAC

ATCTACTGGGACGATGACAAGCGGTATAACCCCTCCCTG

AAGTCTAGACTGACAATCTCTAAGGATACCAGCTCCAAC

CAGGTGTTCCTGAAGATCACAAATGTGGATACCGTGGAC

ACAGCCACCTACTATTGCGCCCGGAGCGCCTACTATTCC

TTTGCCTACTGGGGCCAGGGCACACTGGTGTCTGTGAGC

GCC

The amino acid sequence of the heavy chain variable region of antibody 3H6H1L1 is as follows: (118 aa, in which the underlined amino acid sequences are CDR regions)

(SEQ ID NO: 6)
QVTLKESGPALLKPTQTLTLTCTFS<u>GFSLSTSGMG</u>VSWI

RQPSGKALEWLAH<u>IYWDDDKRYNPSLKS</u>RLTISKDTSSN

QVFLKITNVDTVDTATYYC<u>ARSAYYSFAY</u>WGQGTLVSVS

A

The nucleotide sequence encoding the light chain variable region of antibody 3H6H1L1:

(318 bp)
(SEQ ID NO: 7)
GATATCCAGATGACCCAGTCCCACAGCTCCATGTCCACA

TCTGTGGGCGACCGGGTGAGAATCACCTGTCGGGCCTCC

CAGGACGTGGATACAGACGTGGCCTGGTTTCAGCAGAAG

CCCGGCCAGGCCCCTAAGCTGCTGATCTACTGGGCCAGC

ACCAGGCACTCCGGAGTGCCATCTCGCTTCAGCGGCTCC

GGCTCTGGCACAGACTTCACCCTGACAATCAGCAACGTG

CAGCCAGAGGATTTCGCCGACTACTATTGCCAGCAGTAC

TCTAGCTATCCCACCTTTGGCGCCGGCACAAAGCTGGAG

CTGAAG

The amino acid sequence of the light chain variable region of antibody 3H6H1L1 is as follows: (106 aa, in which the underlined amino acid sequences are CDR regions)

(SEQ ID NO: 8)
DIQMTQSHSSMSTSVGDRVRITCRAS<u>QDVDTDVA</u>WFQQK

PGQAPKW<u>YWAS</u>TRHSGVPSRFSGSGSGTDFTLTISNVQP

EDFADYYC<u>QQYSSYPT</u>FGAGTKLELK (2) Humanized Monoclonal Antibody 3H6H2L2

The nucleotide sequence encoding the heavy chain variable region of antibody 3H6H2L2:

(354 bp)
(SEQ ID NO: 9)
CAGGTGACACTGAAGGAGTCCGGCCCCGCCCTGGTGAAGCC

TACCCAGACACTGACCCTGACATGTACCTTCAGCGGCTTTT

CTCTGAGCACCTCCGGCATGGGCGTGTCCTGGATCAGGCAG

CCATCTGGCAAGGCCCTGGAGTGGCTGGCCCACATCTACTG

GGACGATGACAAGCGGTATTCTCCCAGCCTGAAGTCTAGAC

TGACAATCAGCAAGGATACCAGCTCCAACCAGGTGTTCCTG

ACAATCACCAACGTGGACCCCGTGGACACAGCCACCTACTA

TTGCGCCCGGAGCGCCTACTATTCCTTTGCCTACTGGGGCC

AGGGCACACTGGTGTCCGTGTCTGCC

The amino acid sequence of the heavy chain variable region of antibody 3H6H2L2 is as follows: (118 aa, in which the underlined amino acid sequences are CDR regions)

(SEQ ID NO: 10)
QVTLKESGPALVKPTQTLTLTCTFS<u>GFSLSTSGMG</u>VSWIRQP

SGKALEWLAH<u>IYWDDDKRYSPSLKSRLTISKDTSSNQVFLTI</u>

TNVDPVDTATYYC<u>ARSAYYSFAY</u>WGQGTLVSVSA

The nucleotide sequence encoding the light chain variable region of antibody 3H6H2L2:

(318 bp)
(SEQ ID NO: 11)
GATATCCAGATGACACAGAGCCCTAGCTCCCTGAGCGCCTCC

GTGGGCGACCGGGTGAGAATCACCTGTAGGGCCTCTCAGGAC

GTGGATACAGACGTGGCCTGGTACCAGCAGAAGCCCGGCAAG

GCCCCTAAGCTGCTGATCTATTGGGCCTCTACCCTGCAGAGC

GGAGTGCCATCCCGGTTCTCTGGCAGCGGCTCCGGAACAGAC

TTCACCCTGACAATCTCTAGCCTGCAGCCAGAGGACTTCGCC

ACCTACTATTGCCAGCAGTACTCCTCTTATCCCACCTTTGGC

GCCGGCACAAAGCTGGAGCTGAAG

The amino acid sequence of the light chain variable region of antibody 3H6H2L2 is as follows: (106 aa, in which the underlined amino acid sequences are CDR regions)

(SEQ ID NO: 12)
DIQMTQSPSSLSASVGDRVRITCRAS<u>QDVDTDVA</u>WYQQK

PGKAPKLLIY<u>WAS</u>TLQSGVPSRFSGSGSGTDFTLTISSL

QPEDFATYYC<u>QQYSSYPT</u>FGAGTKLELK (3) Humanized Monoclonal Antibody 3H6H3L3

The nucleotide sequence encoding the heavy chain variable region of antibody 3H6H3L3:

(354 bp)
(SEQ ID NO: 13)
CAGGTGACACTGAAGGAGAGCGGCCCAGCCCTGGTGAAGCCA

ACCCAGACACTGACCCTGACATGTACCTTCTCCGGCTTTAGC

CTGTCCACCTCTGGCATGGGCGTGTCTTGGATCAGGCAGCCA

CCTGGCAAGGCCCTGGAGTGGCTGGCCCTGATCTACTGGGAC

GATGACAAGCGGTATAGCCCTTCCCTGAAGAGCAGACTGACA

ATCTCCAAGGATACCTCTAAGAACCAGGTGGTGCTGACAATC

ACCAACGTGGACCCCGTGGACACAGCCACCTACTATTGCGCC

CGGAGCGCCTACTATTCCTTTGCCTACTGGGGCCAGGGCACA

CTGGTGTCTGTGAGCGCC

The amino acid sequence of the heavy chain variable region of antibody 3H6H3L3 is as follows: (118 aa, in which the underlined amino acid sequences are CDR regions)

(SEQ ID NO: 14)
QVTLKESGPALVKPTQTLTLTCTFS<u>GFSLSTSGMG</u>VSWIRQP

PGKALEWLAL<u>IYWDDDKRYSPSLKSRLTISKDTSKNQVVLTI</u>

TNVDPVDTATYYC<u>ARSAYYSFAY</u>WGQGTLVSVSA

The nucleotide sequence encoding the light chain variable region of antibody 3H6H3L3:

(318 bp)
(SEQ ID NO: 15)
GATATCCAGATGACACAGAGCCCTAGCTCCCTGAGCGCCTCCG

TGGGCGACAGGGTGACCATCACATGTAGAGCCTCTCAGGACGT

GGATACCGACCTGGCCTGGTACCAGCAGAAGCCCGGCAAGGCC

CCTAAGCTGCTGATCTATTGGGCCTCTACCCTGCAGAGCGGAG

TGCCATCCCGGTTCTCTGGCAGCGGCTCCGGAACAGACTTCAC

CCTGACAATCTCTAGCCTGCAGCCAGAGGACTTCGCCACCTAC

TATTGCCAGCAGTACTCCTCTTATCCCACCTTTGGCGCCGGCA

CAAAGCTGGAGCTGAAG

The amino acid sequence of the light chain variable region of antibody 3H6H3L3 is as follows: (106 aa, in which the underlined amino acid sequences are CDR regions)

(SEQ ID NO: 16)
DIQMTQSPSSLSASVGDRVTITCRAS<u>QDVDTDL</u>AWYQQKPGKAP

KLLIY<u>WAS</u>TLQSGVPSRFSGSGSGTDFTLTISSLQPEDFATYYC

<u>QQYSSYPT</u>FGAGTKLELK (4) Humanized Monoclonal Antibody 3H6H4L1

The nucleotide sequence encoding the heavy chain variable region of antibody 3H6H4L1 is set forth in SEQ ID NO: 5.

The amino acid sequence of the heavy chain variable region of antibody 3H6H4L1 is set forth in SEQ ID NO: 6.

The nucleic acid sequence encoding the light chain variable region of antibody 3H6H4L1 is set forth in SEQ ID NO: 7.

The amino acid sequence of the light chain variable region of antibody 3H6H4L1 is set forth in SEQ ID NO: 8.

2. Preparation of Humanized Antibodies 3H6H1L1, 3H6H2L2, 3H6H3L3, and 3H6H4L1

The heavy chain constant regions of 3H6H1L1, 3H6H2L2, and 3H6H3L3 are Ig gamma-1 chain C region, ACCESSION: P01857; and the light chain constant regions are Ig kappa chain C region, ACCESSION: P01834;

the heavy chain constant region of 3H6H4L1 is Ig gamma-4 chain C region, ACCESSION: P01861.1; and the light chain constant region is Ig kappa chain C region, ACCESSION: P01834.

Each of heavy and light chain cDNAs of 3H6H1L1, 3H6H2L2, 3H6H3L3, and 3H6H4L1 was cloned into a pUC57simple vector (provided by Genscript) to give 8 recombinant plasmids respectively, namely pUC57simple-3H6H1 and pUC57simple-3H6L1; pUC57simple-3H6H2 and pUC57simple-3H6L2; pUC57simple-3H6H3 and pUC57simple-3H6L3; and pUC57simple-3H6H4 and pUC57simple-3H6L1. And those were subcloned into pcDNA3.1 vectors, respectively. The recombinant plasmids comprising a heavy chain and the recombinant plasmids comprising a light chain were co-transfected into 293F cells, then the cell culture was collected and purified to give humanized antibodies 3H6H1L1, 3H6H2L2, 3H6H3L3, and 3H6H4L1. The results were qualified by SDS-PAGE.

Example 4. Assay on Binding Activity of Antibodies 3H6, 3H6H1L1, 3H6H2L2, 3H6H3L3, and 3H6H4L1 to Human IL-1β-His-Bio (ELISA)

A plate was coated with 50 μL of 2 μg/mL SA (streptavidin) in each well, and incubated overnight at 4° C. After the plate was washed once and the residual liquid was removed, each well was blocked with 300 μL of 1% BSA solution (dissolved in PBS) and the plate was incubated at 37° C. for 2 h. The plate was washed three times and the residual liquid was removed. Human IL-1β-His-Bio in each well was diluted with 50 μL of PBST to 0.2 μg/mL, and the plate was incubated at 37° C. for 30 min. Then the plate was washed three times and the residual liquid was removed. The antibody was diluted to 1 μg/mL in Table 1 or 0.333 μg/mL in Table 2 as the initial concentration, and a 1:3 gradient dilution was performed to give a total of 7 concentrations, in addition to a blank control. Two duplicate wells were set for the above concentrations, with a final volume of 100 μL per well, and the plate was incubated at 37° C. for 30 min. After the plate was washed three times and patted to remove the residual liquid, 50 μL of horseradish peroxidase-labeled goat anti-human IgG (H+L) secondary antibody working solution or horseradish peroxidase-labeled goat anti-mouse IgG (H+L) secondary antibody working solution was added to each well, and the plate was incubated for 30 min at 37° C., in which, 50 μL of horseradish peroxidase-labeled goat anti-human IgG (H+L) secondary antibody working solution was added to the wells containing 3H6H1L1, 3H6H2L2, 3H6H3L3, 3H6H4L1, canakinumab; and 50 μL of horseradish peroxidase-labeled goat anti-mouse IgG (H+L) secondary antibody working solution was added to the wells containing 3H6. After the plate was washed four times and the residual liquid was removed, 50 μL of TMB chromogenic solution was added to each well for color developing for 5 min away from light at room temperature, then 50 μL of stop solution was added to each well to stop the reaction. Then the plate was put into a plate reader immediately, and the OD value of each well in the plate was read at 450 nm.

Figure 2:
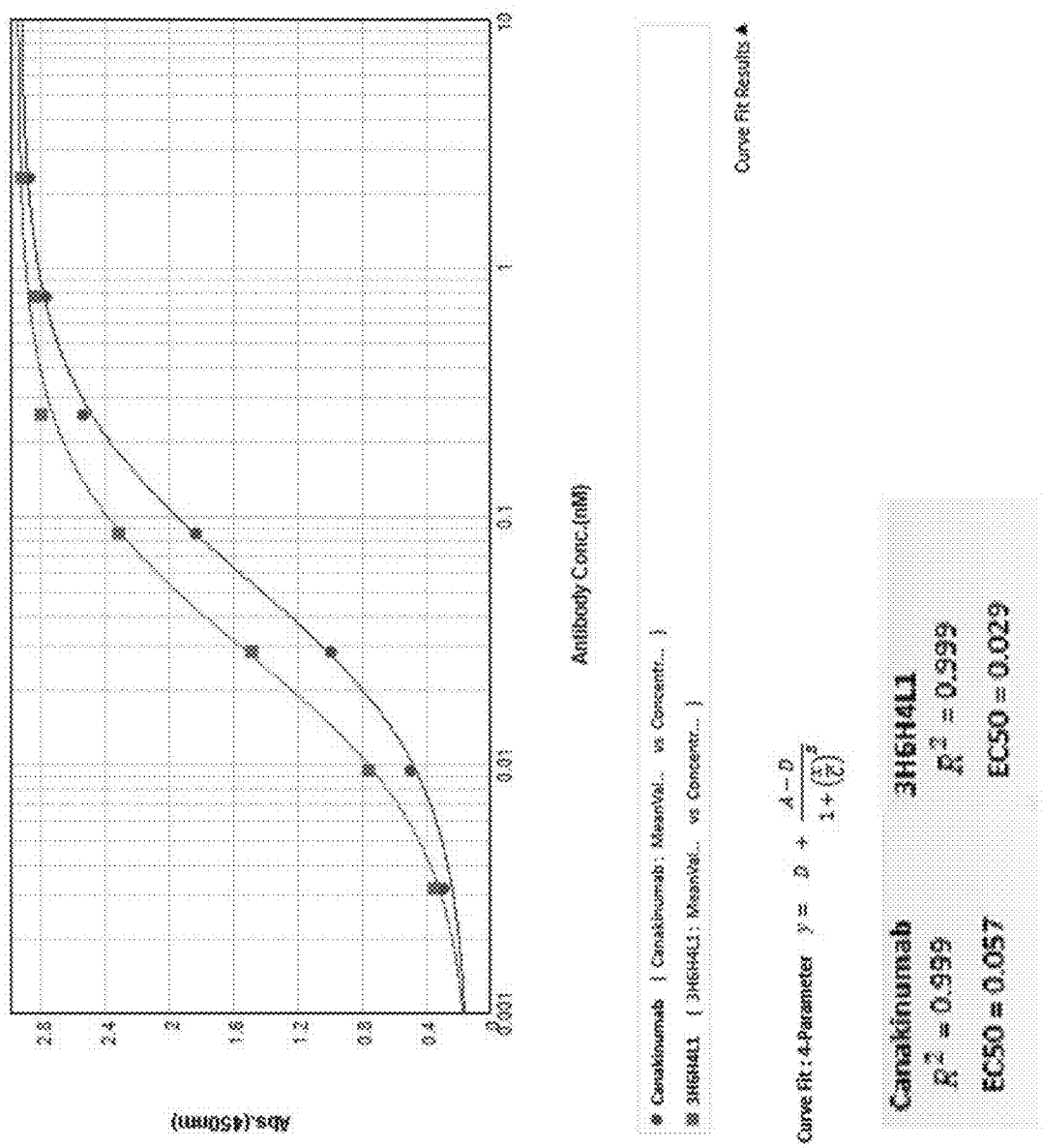
FIG. 2. Assay results of the binding activity of 3H6H4L1 to human IL-1β-His-Bio.

SoftMax Pro 6.2.1 software was used to analyze and process the data. 4-parameter fitted curves were plotted using the antibody concentration as the abscissa and the absorbance as the ordinate. The results are shown in FIGS. 1 and 2. The assay results of the binding activity of 3H6, 3H6H1L1, 3H6H2L2, 3H6H3L3, and 3H6H4L1 to human IL-1β-His-Bio are shown in Tables 1 and 2, respectively.

TABLE 1

Assay results of the binding activity of 3H6, 3H6H1L1, 3H6H2L2, and 3H6H3L3 to human IL-1β-His-Bio

| Antibody concentration (μg/mL) | 3H6H1L1 | | 3H6H2L2 | | 3H6H3L3 | | 3H6 | | Canakinumab | |
|---|---|---|---|---|---|---|---|---|---|---|
| 1 | 2.914 | 2.927 | 2.864 | 2.879 | 2.865 | 2.905 | 2.516 | 2.602 | 2.871 | 2.874 |
| 0.333 | 2.979 | 2.980 | 2.953 | 2.928 | 2.880 | 2.874 | 2.617 | 2.597 | 2.902 | 2.883 |
| 0.111 | 2.950 | 2.989 | 2.958 | 2.953 | 2.892 | 2.865 | 2.411 | 2.386 | 2.895 | 2.887 |
| 0.037 | 2.809 | 2.771 | 2.777 | 2.732 | 2.634 | 2.662 | 2.036 | 1.936 | 2.643 | 2.682 |
| 0.012 | 2.167 | 2.267 | 2.197 | 2.182 | 2.001 | 2.016 | 1.225 | 1.225 | 2.065 | 2.118 |
| 0.004 | 1.352 | 1.264 | 1.300 | 1.439 | 1.225 | 1.178 | 0.598 | 0.623 | 1.256 | 1.199 |
| 0.001 | 0.660 | 0.619 | 0.630 | 0.669 | 0.590 | 0.566 | 0.287 | 0.293 | 0.581 | 0.559 |
| 0 | 0.042 | 0.042 | 0.041 | 0.041 | 0.050 | 0.039 | 0.039 | 0.041 | 0.039 | 0.040 |
| Second antibody | HRP goat anti-human IgG (H + L), 50 μL | | | | | | HRP goat anti-mouse IgG (H + L), 50 μL | | HRP goat anti-human IgG (H + L), 50 μL | |
| $EC_{50}$ (nM) | 0.036 | | 0.034 | | 0.042 | | 0.099 | | 0.039 | |

TABLE 2

Assay results of the binding activity of 3H6H4L1 to human IL-1β-His-Bio

| Antibody dilution | Antigen-antibody binding OD (450 nm) value | |
|---|---|---|
| | Canakinumab | 3H6H4L1 |
| 0.333 μg/mL | 2.809  2.940 | 2.899  2.935 |
| 1:3 | 2.679  2.875 | 2.822  2.866 |
| 1:9 | 2.463  2.613 | 2.814  2.797 |
| 1:27 | 1.702  1.959 | 2.311  2.322 |
| 1:81 | 0.852  1.115 | 1.525  1.436 |
| 1:243 | 0.408  0.573 | 0.771  0.737 |
| 1:729 | 0.315  0.242 | 0.358  0.332 |
| 0 | 0.075  0.071 | 0.071  0.075 |
| Second antibody | HRP goat anti-human IgG (H + L), 50 μL | |
| $EC_{50}$ (nM) | 0.057 | 0.029 |

The results showed that 3H6, 3H6H1L1, 3H6H2L2, 3H6H3L3 and 3H6H4L1 can effectively bind to the human IL-1β-His-Bio with the binding efficiency being dose-dependent. Under the same assay condition, the binding efficiency of 3H6H1L1, 3H6H2L2, and 3H6H4L1 to the antigen human IL-1β-His-Bio is dose-dependent, and the binding activity is superior to that of the marketed drug canakinumab for the same target; while the binding activity of 3H6H3L3 is comparable to that of canakinumab.

Example 5. Assay on Activity of Antibodies 3H6, 3H6H1L1, 3H6H2L2, 3H6H3L3, and 3H6H4L1 Competing with Human IL-1R1 (1-332)-His for Binding to Human IL-1β-hFc (ELISA)

A plate was coated with 50 μL of 4 μg/mL human IL-1β-hFc in each well, and incubated overnight at 4° C. After the plate was washed once and the residual liquid was removed, each well was blocked with 300 μL of 1% BSA solution (dissolved in PBS) and the plate was incubated at 37° C. for 2 h. Then the plate was washed three times and the residual liquid was removed. The antibody was diluted to 2 μg/mL (final concentration: 1 μg/mL) as the initial concentration, and a 1:3 gradient dilution was performed to give a total of 7 concentrations, in addition to a blank control. Two duplicate wells were set for the above concentrations, with a final volume of 50 μL per well, and the plate was incubated for 10 min. 50 μL of 0.08 μg/mL (final concentration: 0.04 μg/mL) or 0.1 μg/mL (final concentration: 0.05 μg/mL) human IL-1R1 (1-332)-his was added to each well in the plate, gently mixed with the antibody at a volume ratio of 1:1, with the final volume of each well being 100 μL. Then the plate was incubated at 37° C. for 30 min. After the plate was washed three times and the residual liquid was removed, 50 μL of anti-His murine monoclonal antibody (HRP-labeled) working solution was added to each well, and the plate was incubated at 37° C. for 30 min. After the plate was washed four times and the residual liquid was removed, 50 μL of TMB chromogenic solution was added to each well for color developing for 10 min or 5 min away from light at room temperature, then 50 μL of stop solution was added to each well to stop the reaction. Then the plate was put into a plate reader immediately, and the OD value of each well in the plate was read at 450 nm.

Figure 3:
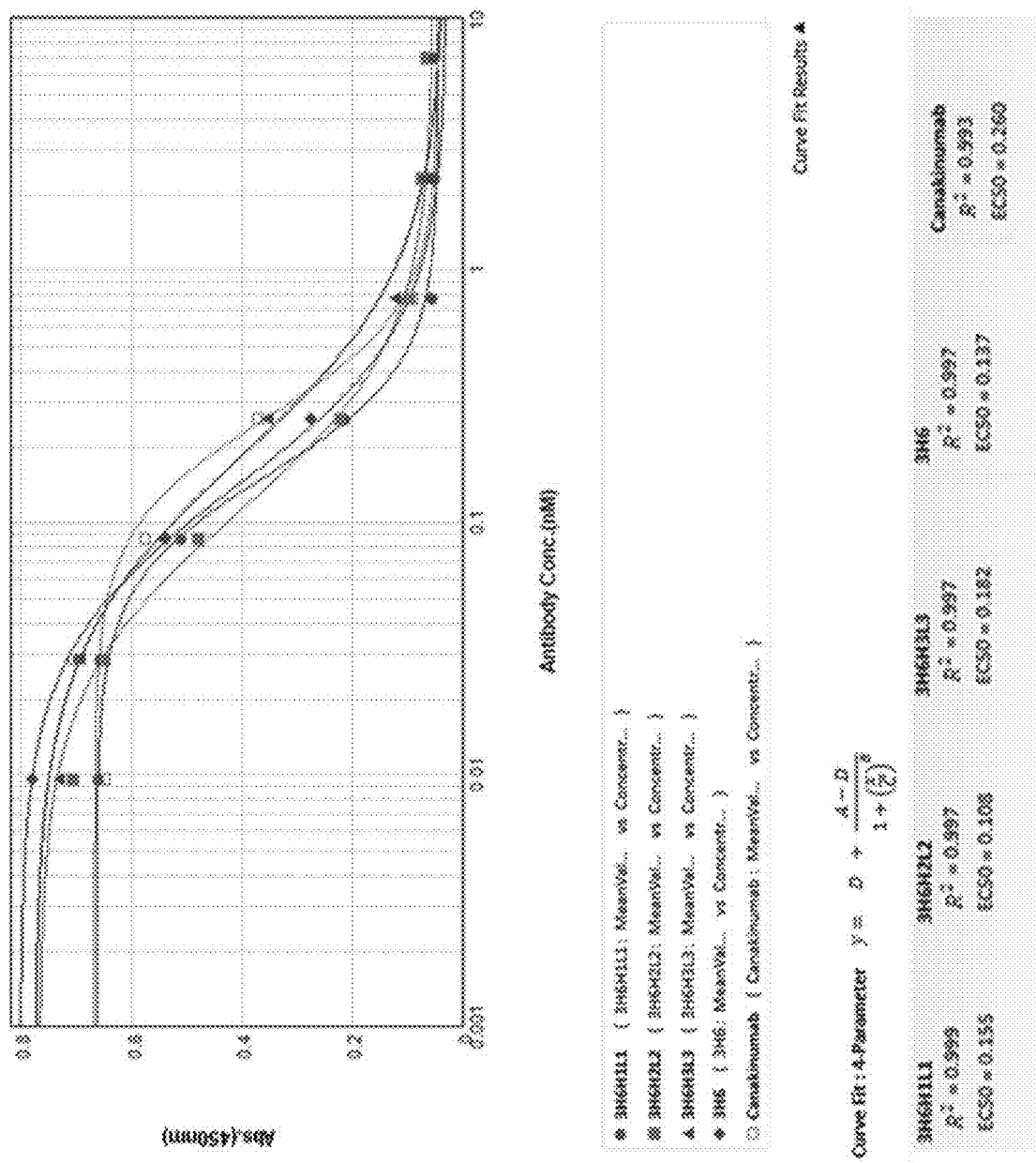
FIG. 3. Assay results of the activity of 3H6, 3H6H1L1, 3H6H2L2, and 3H6H3L3 competing with human IL-1R1 (1-332)-His for binding to human IL-1β-hFc.
Figure 4:
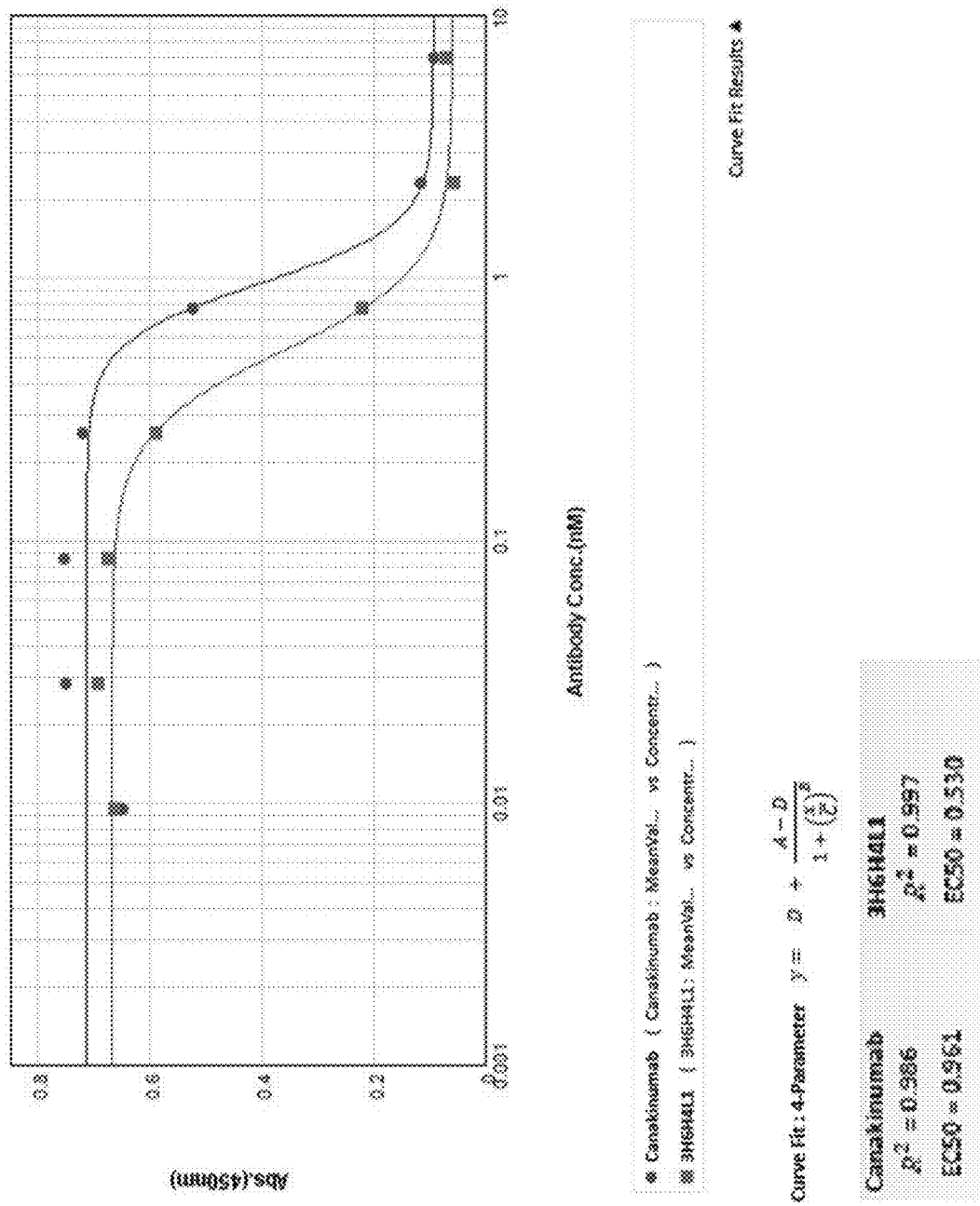
FIG. 4. Assay results of the activity of 3H6H4L1 competing with human IL-1R1 (1-332)-His for binding to human IL-1β-hFc.

The data were analyzed and processed using SoftMax Pro 6.2.1 software and 4-parameter fit curves were plotted using the antibody concentration as the abscissa and the absorbance as the ordinate. The results are shown in FIGS. 3 and 4. The assay results of the activity of 3H6, 3H6H1L1, 3H6H2L2, 3H6H3L3, and 3H6H4L1 competing with human IL-1R1 (1-332)-his for binding to human IL-1β-hFc are shown in Tables 3 and 4, respectively.

TABLE 4

Assay results of the activity of 3H6H4L1 competing with human IL-1R1(1-332)-his for binding to human IL-1β-hFc

| Antibody concentration (μg/mL) | OD (450 nm) value of the antibody blocking the binding of the antigen to the receptor human IL-1R1(1-332)-his | | | |
|---|---|---|---|---|
| | Canakinumab | | 3H6H4L1 | |
| 1.000 | 0.093 | 0.088 | 0.079 | 0.063 |
| 0.333 | 0.104 | 0.126 | 0.055 | 0.055 |
| 0.111 | 0.519 | 0.526 | 0.239 | 0.201 |
| 0.037 | 0.736 | 0.705 | 0.629 | 0.547 |
| 0.012 | 0.797 | 0.706 | 0.701 | 0.648 |
| 0.004 | 0.765 | 0.735 | 0.710 | 0.673 |
| 0.001 | 0.738 | 0.559 | 0.666 | 0.662 |
| 0.000 | 0.669 | 0.719 | 0.659 | 0.621 |
| EC$_{50}$ (nM) | 0.961 | | 0.530 | |

The results showed that 3H6, 3H6H1L1, 3H6H2L2, 3H6H3L3, and 3H6H4L1 can effectively block the binding of the antigen human IL-1β-hFc to the receptor human IL-1R1 (1-332)-his with the blocking efficiency being dose-dependent, and their competitive binding activity is superior than that of the marketed drug canakinumab for the same target.

Example 6. Determination of Affinity Constant of Antibody 3H6H4L1 for Human IL-1β

Figure 5:
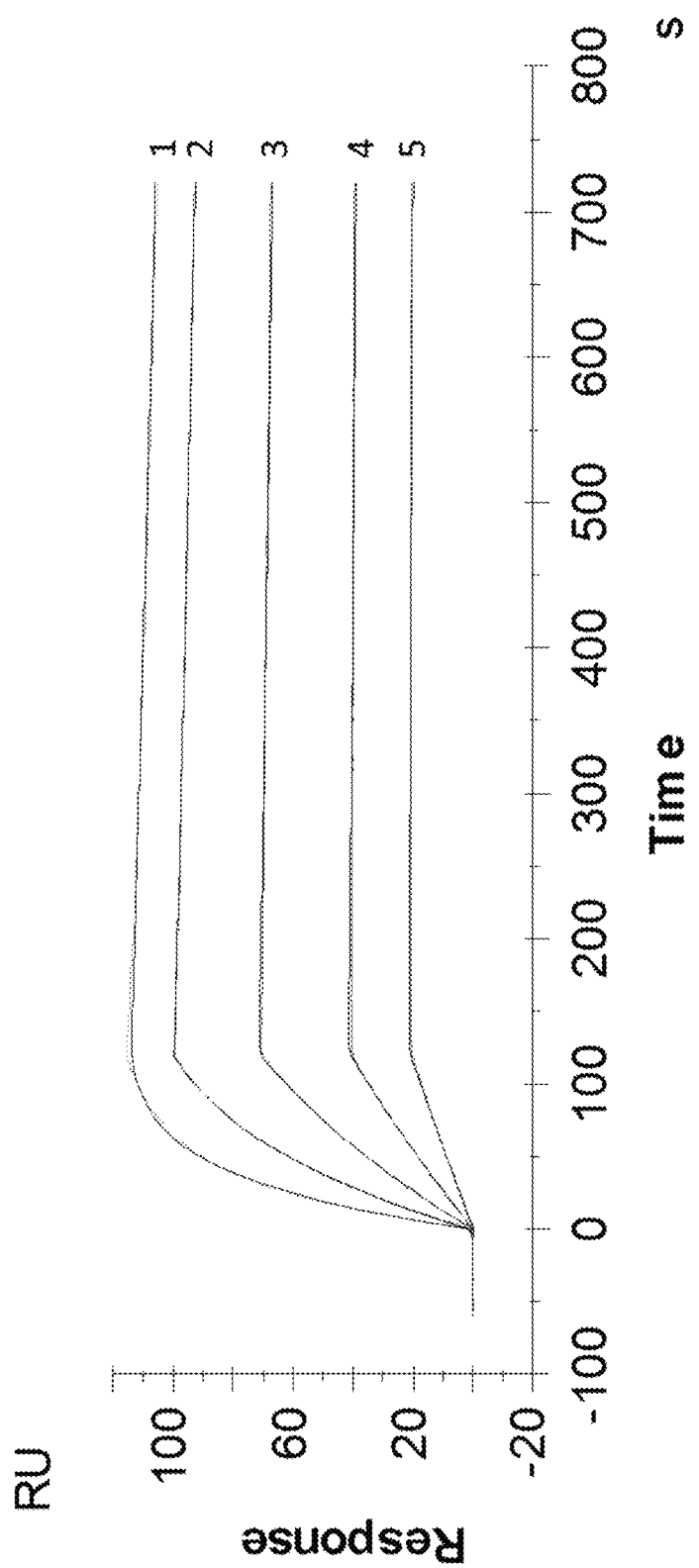
FIG. 5. Assay results of affinity constant of 3H6H4L1 for human IL-1β. Note: curves 1-5 show the analyte concentrations at 25 nM, 12.5 nM, 6.25 nM, 3.13 nM, and 1.56 nM, respectively.
Figure 6:
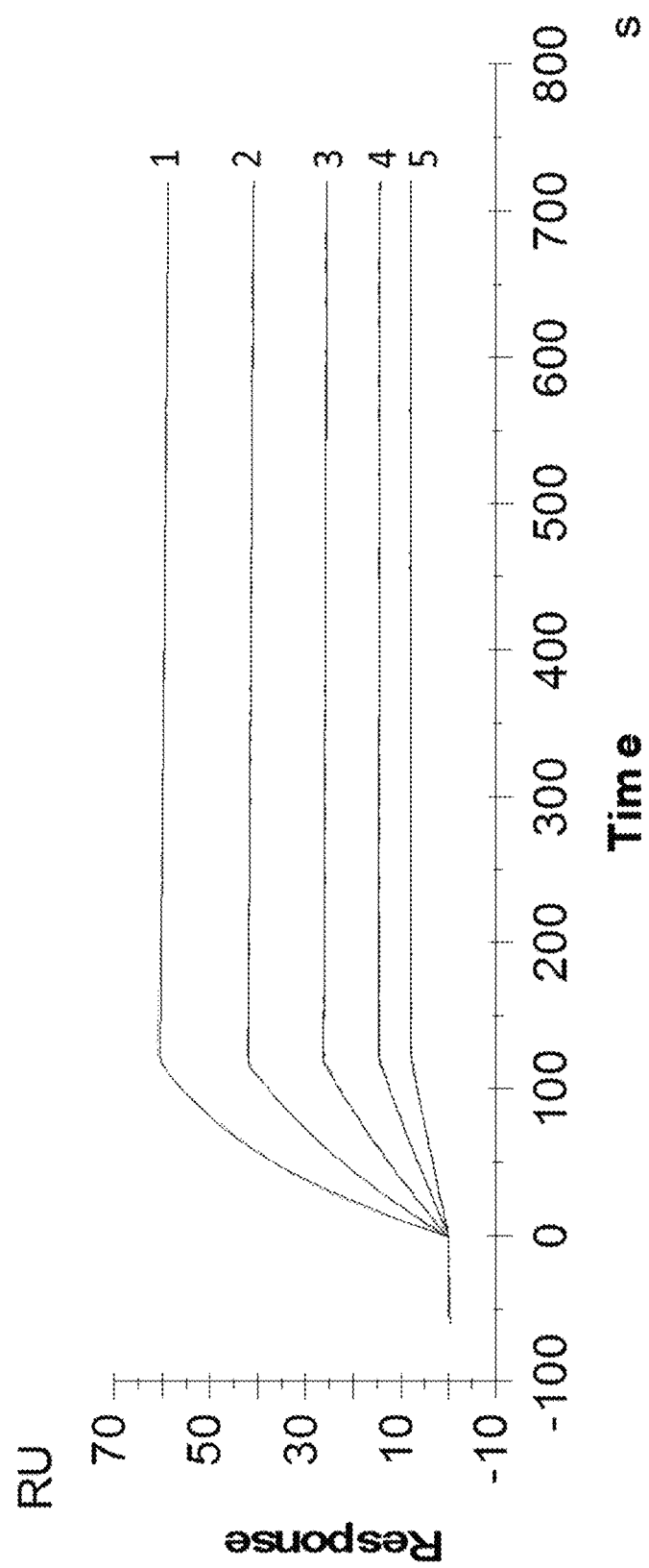
FIG. 6. Assay results of affinity constant of Canakinumab for human IL-1β. Note: curves 1-5 show the analyte concentrations at 25 nM, 12.5 nM, 6.25 nM, 3.13 nM, and 1.56 nM, respectively.

The affinity constant of the antibody for the human IL-1β-his was determined using a Biacore molecular interaction instrument. The antibody was immobilized on the surface of CM5 chip in a PBST buffer by amine coupling, with a signal value of about 1000 RU. The antibody bound to human IL-1β at a concentration of 1.56-25 nM (2-fold gradient dilution) for 120 s at a flow rate of 30 μL/min, and they were dissociated for 600 s. The chip was regenerated using 3M MgCl$_2$ for 30 s at a flow rate of 30 μL/min. Data was acquired using Biacore Control 2.0 software and analyzed using Biacore T200 Evaluation 2.0 software. The results are shown in Table 5, FIG. 5 and FIG. 6.

TABLE 3

Assay results of the activity of 3H6, 3H6H1L1, 3H6H2L2, and 3H6H3L3 competing with human IL-1R1(1-332)-his for binding to human IL-1β-hFc

| Antibody concentration (μg/mL) | OD (450 nm) value of the antibody blocking the binding of the antigen to the receptor human IL-1R1(1-332)-his | | | | | | | | | |
|---|---|---|---|---|---|---|---|---|---|---|
| | 3H6H1L1 | | 3H6H2L2 | | 3H6H3L3 | | 3H6 | | Canakinumab | |
| 1.000 | 0.050 | 0.049 | 0.057 | 0.070 | 0.057 | 0.058 | 0.049 | 0.050 | 0.053 | 0.052 |
| 0.333 | 0.051 | 0.050 | 0.071 | 0.073 | 0.069 | 0.067 | 0.050 | 0.052 | 0.059 | 0.057 |
| 0.111 | 0.055 | 0.054 | 0.095 | 0.098 | 0.132 | 0.115 | 0.063 | 0.058 | 0.091 | 0.092 |
| 0.037 | 0.206 | 0.221 | 0.242 | 0.198 | 0.361 | 0.348 | 0.266 | 0.283 | 0.366 | 0.379 |
| 0.012 | 0.521 | 0.498 | 0.504 | 0.453 | 0.505 | 0.584 | 0.560 | 0.516 | 0.572 | 0.579 |
| 0.004 | 0.635 | 0.677 | 0.681 | 0.618 | 0.693 | 0.697 | 0.682 | 0.712 | 0.727 | 0.684 |
| 0.001 | 0.630 | 0.687 | 0.736 | 0.679 | 0.748 | 0.715 | 0.787 | 0.773 | 0.577 | 0.720 |
| 0.000 | 0.621 | 0.693 | 0.804 | 0.779 | 0.780 | 0.807 | 0.810 | 0.818 | 0.555 | 0.765 |
| EC$_{50}$ (nM) | 0.155 | | 0.108 | | 0.182 | | 0.137 | | 0.260 | |

TABLE 5

Assay results of the affinity constant of 3H6H4L1 for human IL-1β

| Name | $K_D$ (M) | ka (1/Ms) | SE (ka) | kd (1/s) | SE (kd) | Rmax (RU) |
|---|---|---|---|---|---|---|
| 3H6H4L1 | 8.79E−11 | 1.44E+06 | 3.15E+03 | 1.27E−04 | 1.75E−07 | 112.49-122.37 |
| Canakinumab | 9.79E−11 | 5.24E+05 | 6.84E+02 | 5.13E−05 | 1.43E−07 | 76.61-86.37 |

The results showed that the affinity constant of 3H6H4L1 for human IL-1β was 8.79E-11M, and the affinity constant of Canakinamiab for human IL-1β was 9.79E-11M, suggesting that 3H6H4L1 has stronger binding ability to human IL-1β.

Example 7: Assay on Cell Bioactivity of Antibody 3H6H4L1

1. Cytology Assay on the Activity of 3H6H4L1 Blocking IL-1β for Inducing MRC-5 Cells to Secrete IL-6

Figure 7:
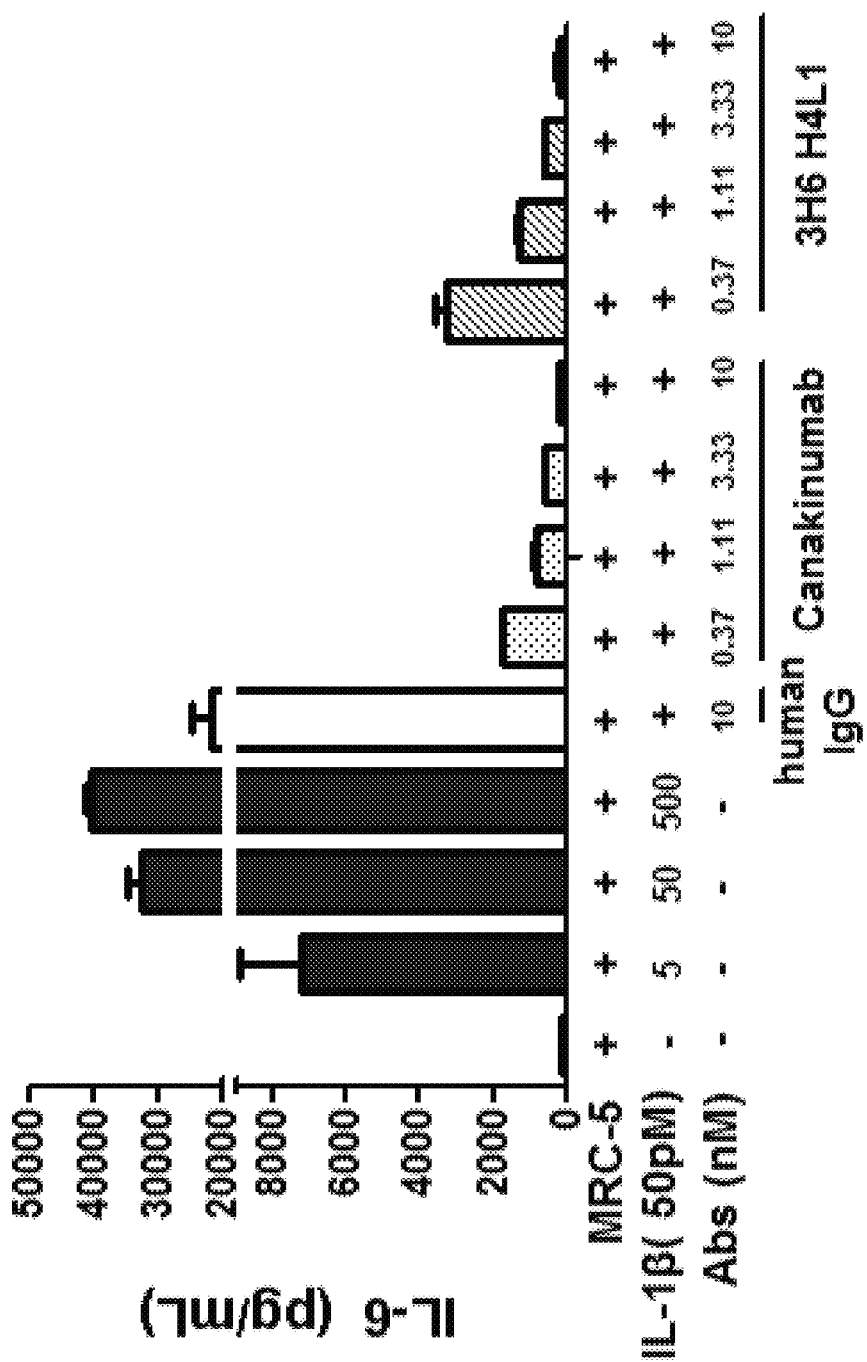
FIG. 7. Effect of 3H6H4L1 on IL-1β-induced secretion of IL-6 by MRC-5.

Human MRC-5 cells (purchased from the Cell Center of the Chinese Academy of Sciences) were digested and counted conventionally, and 7,500 cells/well were seeded into a flat-bottom 96-well plate and cultured in a cell incubator; 24 h later (when cell growth reached 80% confluence), the dosing treatment was carried out: 4 concentrations (0.37 nM, 1.11 nM, 3.33 nM, and 10 nM) were set for antibody and 3 concentrations (5 pM, 50 pM, and 500 pM) were set for of IL-1β (purchased from Sino Biological Inc.), 50 pM IL-1β was used in the antibody group (the antibody and the IL-1β were incubated at 37° C. for 20 min in advance), in addition to a blank control group and an isotype control group; after dosing, the groups were cultured for 24 h; cell supernatants were collected and assayed using IL-6 ELISA Kit (purchased from Dakewe Biotechnology Co., Ltd.). The assay results are shown in FIG. 7 and Table 6.

2. 3H6H4L1 Blocking IL-1β to Activate NF-κB Signaling Pathway

In this experiment, the neutralizing bioactivity of 3H6H4L1 blocking IL-1β to activate NF-κB signaling pathway was measured by luciferase gene reporter assay.

(1) 293T-NF-κB-LUC Cell Construction 293T cells were digested by pancreatin and subcultured; the medium was refreshed by opti-DMEM medium 2 h before transfection; 500 μL of opti-DMEM medium was added to a sterile EP tube, followed by 3 μg of plasmids pNF-κB-Luc2P-hygro; 500 μL of opti-DMEM medium was added to a sterile EP tube, followed by 8 μL of lipofectamine 2000; the diluted lipofectamine 2000 was added to the diluted plasmids, and the mixture was placed at room temperature for 15 min, and uniformly added dropwise to a cell culture dish; 8 h after transfection, the medium was refreshed; and 24 h after transfection, Hygromycin was added and the cells were screened at a final concentration of 100 μg/mL, with the well containing 293T untransfected plasmids as a control. 7-10 days later, the cells in the control well were completely dead, and the screened cells were harvested for amplification. Dosing was continued and the concentration was remained at 100 g/mL. The stable 293T-NF-κB-LUC cell line was obtained.

TABLE 6

Activity of 3H6H4L1 gradiently inhibiting the activity of IL-1β for inducing MRC-5 to secrete IL-6

| Group/ concentration | OD (450 nm) | | Concentration assayed (pg/mL) | | Dilution factor | Original concentration (pg/mL) (concentration assayed × dilution factor) | |
|---|---|---|---|---|---|---|---|
| | Well 1 | Well 2 | Well 1 | Well 2 | | Well 1 | Well 2 |
| PBS | 0.595 | 0.446 | 26.6 | 18.3 | 5 | 132.8 | 91.4 |
| Human IgG/10 nM | 1.301 | 1.476 | 92.8 | 123.9 | 200 | 18552.6 | 24781.8 |
| IL-1β/5 pM | 1.678 | 1.404 | 178.7 | 109.8 | 50 | 8936.3 | 5490.7 |
| IL-1β/50 pM | 1.597 | 1.666 | 153.4 | 174.5 | 200 | 30681.6 | 34898.6 |
| IL-1β/500 pM | 1.207 | 1.228 | 79.6 | 82.4 | 500 | 39817.0 | 41182.0 |
| Canakinumab/0.37 nM | 0.432 | 0.425 | 17.6 | 17.2 | 100 | 1758.0 | 1720.1 |
| Canakinumab/1.11 nM | 0.375 | 0.439 | 14.7 | 17.9 | 50 | 736.3 | 896.3 |
| Canakinumab/3.33 nM | 0.646 | 0.590 | 29.7 | 26.3 | 20 | 594.3 | 525.0 |
| Canakinumab/10 nM | 0.305 | 0.318 | 11.4 | 12.0 | 20 | 227.1 | 239.3 |
| 3H6H4L1/0.37 nM | 1.029 | 1.143 | 59.7 | 71.8 | 50 | 2984.1 | 3591.5 |
| 3H6H4L1/1.11 nM | 1.067 | 1.091 | 63.4 | 66.1 | 20 | 1268.8 | 1321.0 |
| 3H6H4L1/3.33 nM | 0.665 | 0.666 | 30.9 | 30.9 | 20 | 618.0 | 618.5 |
| 3H6H4L1/10 nM | 0.469 | 0.609 | 19.5 | 27.4 | 10 | 195.2 | 274.4 |

The results showed that IL-1β can remarkably promote MRC-5 to secrete IL-6 in a dose-dependent manner; 3H6H4L1 can specifically inhibit the activity of IL-1β for inducing MRC-5 cells to secrete IL-6, showing the specific neutralizing activity of 3H6H4L1 on IL-1β.

(2) Assay on Neutralization Bioactivity of 3H6H4L1 Blocking IL-1β to Activate NF-κB Signaling Pathway 293T-NF-κB-LUC cells were routinely digested and seeded into a 96-well plate at 20,000 cells/well. After the cells were adhered to the wall, IL-1β was added to a final concentration of 1.65 ng/mL, and a blank control was set. Antibodies canakinumab and 3H6H4L1 were added simultaneously, with 5 gradients for each antibody, at final concentrations of 400 ng/ml, 100 ng/ml, 25 ng/mL, 6.25 ng/ml, and 1.56 ng/ml, respectively. After 6 h of co-incubation, the supernatant was removed, 50 μL of PBS and 50 μL of Bright-Glo™ substrate were added to react for 5 min, and the mixture was assayed using the machine.

Figure 8:
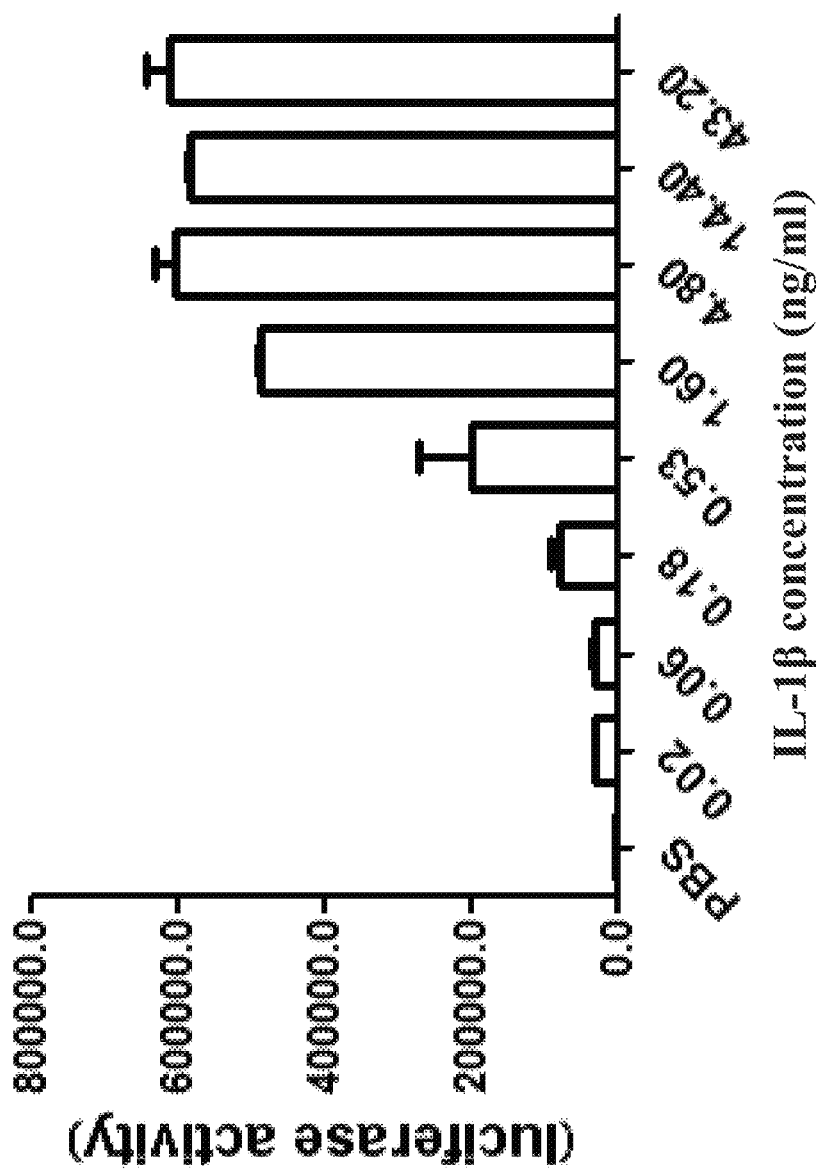
FIG. 8. Effect of IL-1β on gradient activation of NF-κB signaling pathway.
Figure 9:
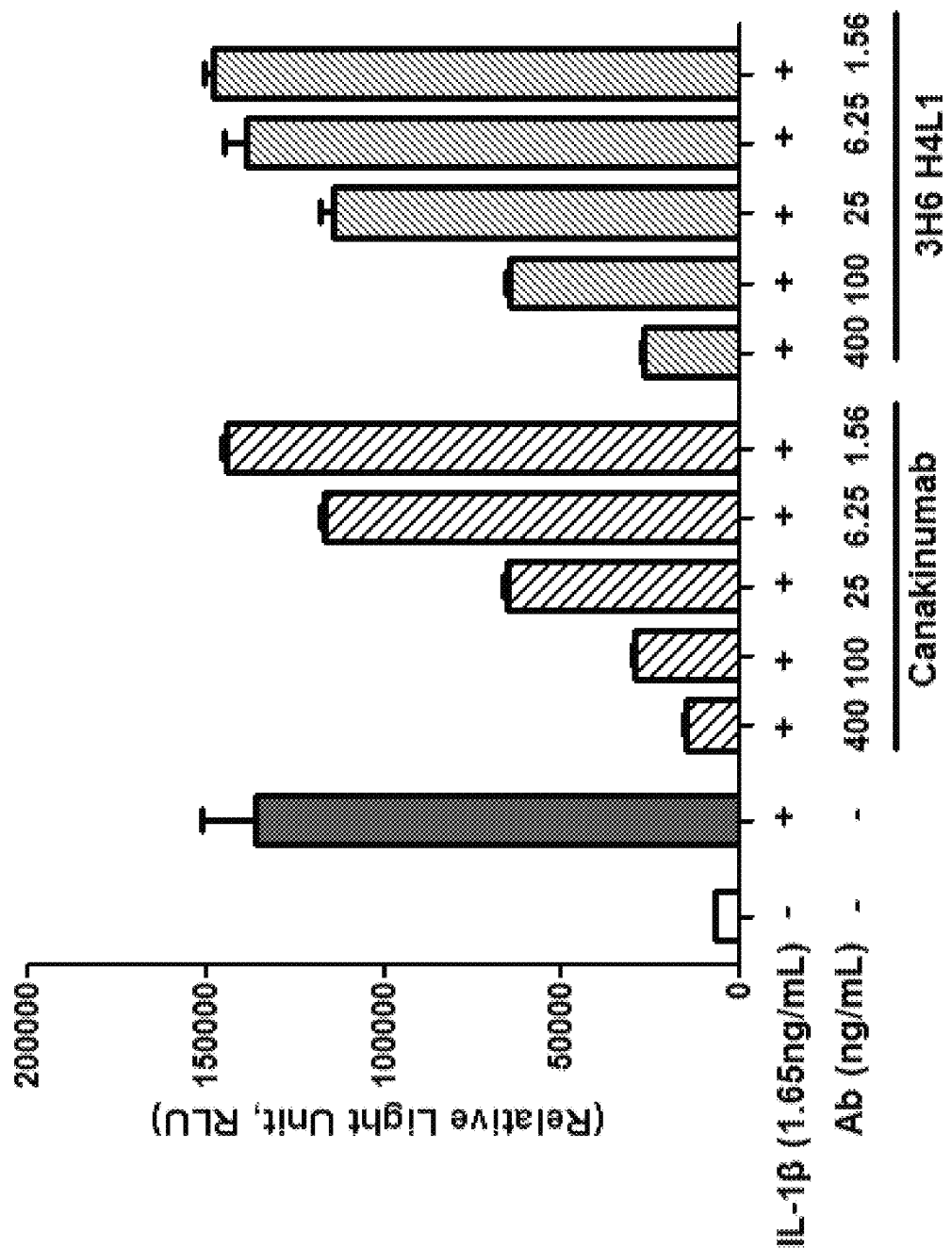
FIG. 9. Reporter assay diagram of 3H6H4L1 blocking IL-1β.

The results are shown in FIGS. 8 and 9.

The results showed that:

IL-1β can effectively activate the expression of luciferase reporter genes dependent on NF-κB signaling pathway in an obvious dose-dependent manner;

3H6H4L1 can specifically block IL-1β to activate NF-κB signaling pathway in a dose-dependent manner.

The results showed that 3H6H4L1 can effectively block IL-1β to activate NF-κB in an IL-1β dependent NF-κB signaling pathway report system, showing its specific neutralizing activity on IL-1β.

Example 8. 3H6H4L1 Alleviating Rheumatoid Knee Arthritis Model Mouse Treatment Induced by NIH/3T3 Cells Transfecting Human IL-1β

46 BALB/c mice were divided into 6 groups by body weight, i.e.:

a normal group, a model group, a positive-control group, a 3H6H4L1 low-dose group, a 3H6H4L1 medium-dose group and a 3H6H4L1 high-dose group; except for 6 mice in the normal group, each group had 8 mice.

Before cell seeding, according to the body weight of mice and the dosing volume, mice were injected subcutaneously with canakinumab in the positive-control group, injected subcutaneously with Anti-HEL in the model group, injected with 3H6H4L1 at corresponding concentrations in the corresponding 3H6H4L1 dose groups, and injected subcutaneously with isovolumetric normal saline.

NIH/3T3 (purchased from American Type Culture Collection) cells and *Lenti*-IL-1β-NIH/3T3 cells were collected in a biosafety cabinet. The *Lenti*-IL-1β-NIH/3T3 cell line that stably secretes and expresses IL-1β was obtained by transfecting a *Lenti*-IL-1β vector into NIH/3T3 cells and screening. When the required number of cells was reached, NIH/3T3, *Lenti*-IL-1β-NIH/3T3 cells were collected. In a biosafety cabinet, stale medium was pipetted, the cells were washed with PBS once and digested with an appropriate amount of 0.05% Trypsin-EDTA (1×) for 1 min, then DMEM complete medium containing 10% FBS was added to stop the digestion. The cell suspension was centrifuged for 4 min at 1200 rpm/min, and after removing the supernatant, resuspended in serum-free DMEM medium and counted, and placed on ice for later use after the cell concentration was adjusted to 2,000,000 cells/mL.

After BALB/c mice was anesthetized by intraperitoneal injection of 7.5 mL/kg of 3.5% chloral hydrate, the knee joint cavities of the mice in the normal group were inoculated with 25 uL/mouse (50,000 cells/mouse) of NIH/3T3 cell suspension, and those of the other mice were inoculated with 25 μL/mouse (50,000 cells/mouse) of *Lenti*-IL-1β-NIH/3T3 cell suspension. After inoculation, the knee joint wound was sutured and applied with 20-fold diluted penicillin in normal saline. On day 5 after the cell inoculation, mice in each group was euthanized by cervical dislocation, the knee joints of the affected limbs were dissected, and the length (mm) and width (mm) of the synovium in the affected limbs of the mice were measured with a vernier caliper. Data were expressed as mean±standard error (±SEM), and results were evaluated by one-way analysis of variance analysis after the inter-group comparison processed by GraphPad Prism 5 software, suggesting a significant difference when $P<0.05$ and a very significant difference when $P<0.01$.

Figure 10:
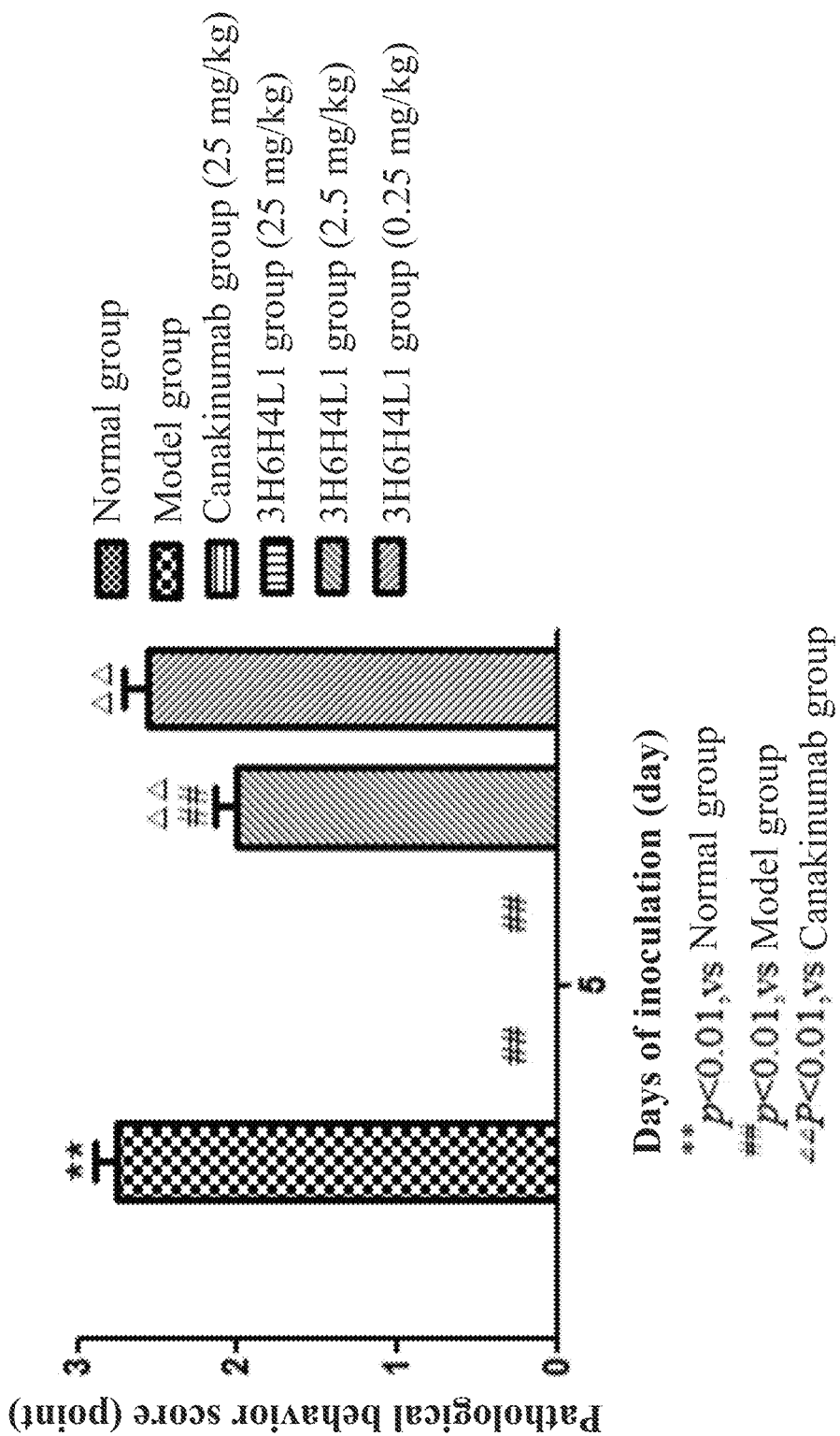
FIG. 10. Effect of 3H6H4L1 on the pathological behavior in *Lenti*-IL-1β-NIH/3T3-induced mouse knee arthritis model.
Figure 11:
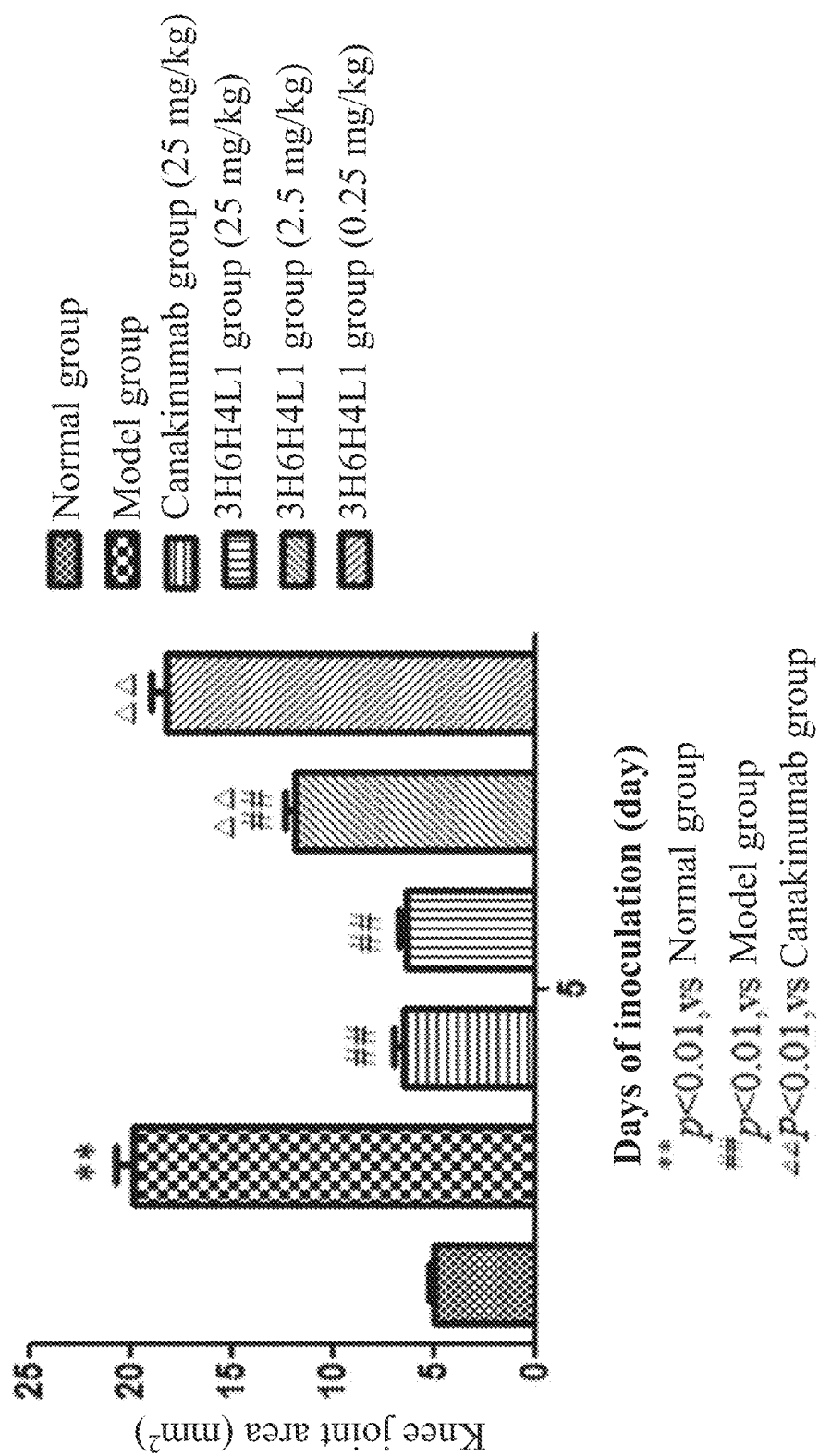
FIG. 11. Effect of 3H6H4L1 on the knee joint area of *Lenti*-IL-1β-NIH/3T3-induced mouse knee arthritis model.
Figure 12:
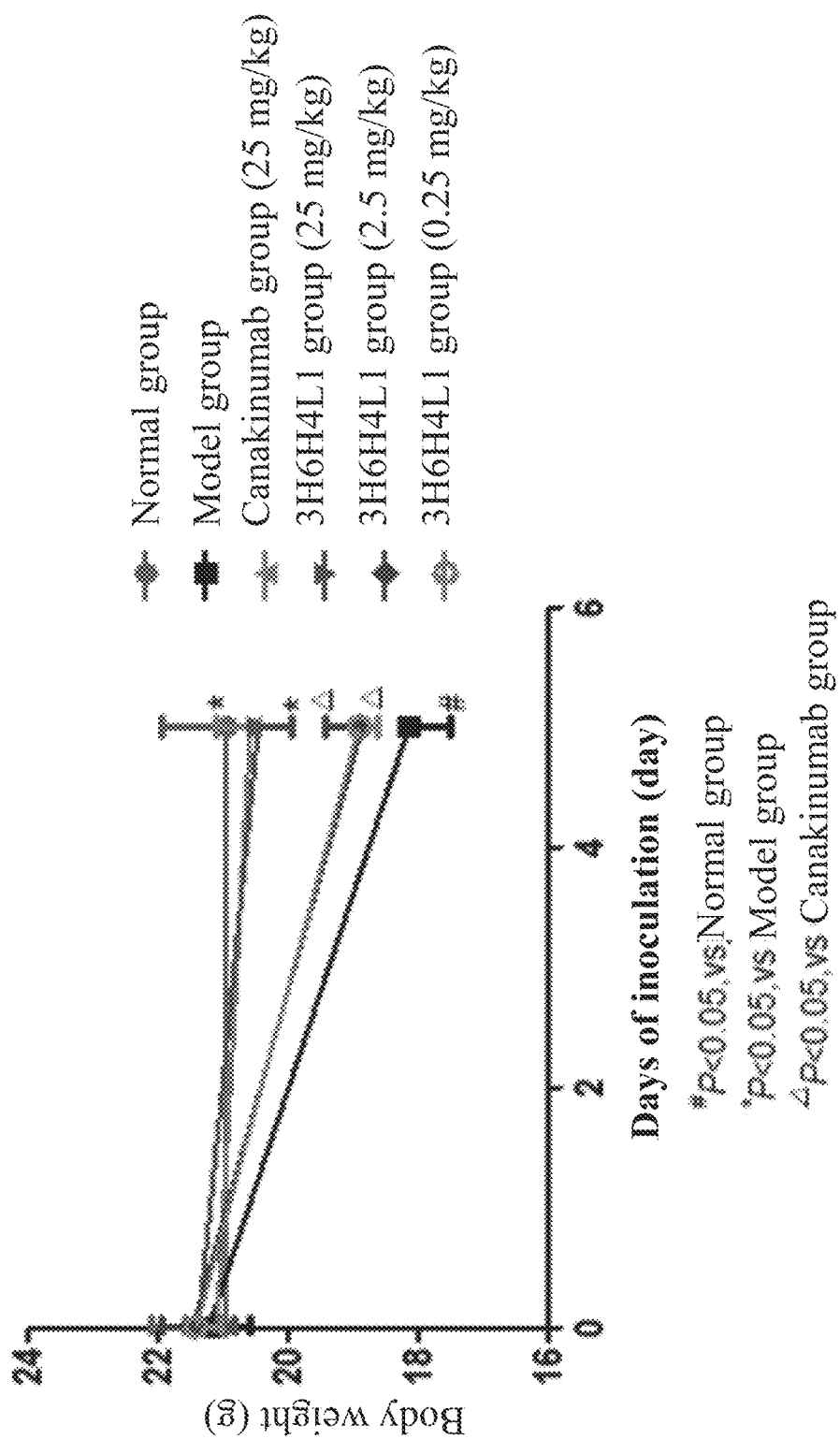
FIG. 12. Effect of 3H6H4L1 on the body weight of *Lenti*-IL-1β-NIH/3T3-induced mouse knee arthritis model.

The results are shown in FIGS. 10, 11, and 12.

FIG. 10 shows that the pathological behavior is evident in the mice of the model group compared to those in the normal group ($P<0.01$). After administration, canakinumab and the 3H6H4L1 high- and medium-dose groups can effectively improve the pathological behaviors of the mice with rheumatoid arthritis ($P<0.01$), while 3H6H4L1 low-dose group is not effective in improving the pathological behaviors of the mice with rheumatoid arthritis ($P>0.05$) compared to the model group. Meanwhile, 3H6H4L1 has a certain dose-effect relationship on improving the pathological behavior degree of the mice. Compared to the positive-control group, the 3H6H4L1 medium- and low-dose groups ($P<0.01$) are less effective than the positive control group, and the 3H6H4L1 high-dose group has efficacy equivalent to that of the positive-control group ($P>0.05$).

FIG. 11 shows that the knee joint area of the affected limb of the mice in the model group is significantly increased compared to the normal group ($P<0.01$). After administration, the positive-control group (canakinumab) and the 3H6H4L1 middle- and high-dose groups can obviously reduce the swelling area of the affected limb of the mice with rheumatoid arthritis ($P<0.01$), while the 3H6H4L1 low-dose group has no obvious effect on reducing the swelling area of the affected limb of the mice with rheumatoid arthritis ($P>0.05$) compared to the model group. Meanwhile, 3H6H4L1 has a certain dose-effect relationship on reducing the swelling area of the affected limb of the mice with rheumatoid arthritis. The equivalent dose of 3H6H4L 1 has efficacy equivalent to the marketed drug canakinumab for the same target ($P>0.05$).

FIG. 12 shows that the body weight of the mice in the model group is significantly reduced compared to that in the normal group ($P<0.01$). After administration, the marketed drug canakinumab for the same target and the 3H6H4L1 high-dose group can obviously reduce the weight loss of the mice with arthritis compared to the model group ($P<0.05$). Compared to the positive-control group, the equivalent dose of 3H6H4L1 has efficacy equivalent to the marketed drug canakinumab for the same target ($P>0.05$).

The preferred embodiments of the present invention have been described above in detail, but the present invention is not limited to the embodiments. Those skilled in the art can make various equivalent modifications or replacements without violating the spirit of the present invention. These equivalent modifications or replacements are included in the scope defined by the claims of the present application.

What is claimed is:

1. A monoclonal anti-IL-1β antibody or antigen-binding fragment thereof, comprising: a) a heavy chain variable region (VH) comprising three complementarity determining regions (HCDRs): HCDR1 having the amino acid sequence set forth in SEQ ID NO: 17, HCDR2 having the amino acid sequence set forth in SEQ ID NO: 18, and HCDR3 having the amino acid sequence set forth in SEQ ID NO: 19; and b) a light chain variable region (VL) comprising three complementarity determining regions (LCDRs): LCDR1 having the amino acid sequence set forth in SEQ ID NO: 20, LCDR2 having the amino acid sequence set forth in SEQ ID NO: 21, and LCDR3 having the amino acid sequence set forth in SEQ ID NO: 22.

2. The monoclonal anti-IL-1β antibody or antigen-binding fragment thereof of claim 1, wherein
the VH comprises the amino acid sequence set forth in SEQ ID NO: 2, and
the VL comprises the amino acid sequence set forth in SEQ ID NO: 4.

3. The monoclonal anti-IL-1β antibody or antigen-binding fragment thereof of claim 1, wherein
the VH comprises the amino acid sequence set forth in SEQ ID NO: 6, and
the VL comprises the amino acid sequence set forth in SEQ ID NO: 8.

4. The monoclonal anti-IL-1β antibody or antigen-binding fragment thereof of claim 1, wherein
the VH comprises the amino acid sequence set forth in SEQ ID NO: 10, and
the VL comprises the amino acid sequence set forth in SEQ ID NO: 12.

5. The monoclonal anti-IL-1β antibody or antigen-binding fragment thereof of claim 1, wherein
the VH comprises the amino acid sequence set forth in SEQ ID NO: 14, and
the VL comprises the amino acid sequence set forth in SEQ ID NO: 16.

6. The monoclonal anti-IL-1β antibody or antigen-binding fragment thereof of claim 1, wherein the monoclonal anti-IL-1β antibody or antigen-binding fragment thereof is selected from an Fab, an Fab', an F(ab')2, an Fv, a single chain antibody, a humanized antibody, a chimeric antibody, and a diabody.

7. The monoclonal anti-IL-1β antibody or antigen-binding fragment thereof of claim 1, wherein the monoclonal anti-IL-1β antibody or antigen-binding fragment thereof binds to IL-1β protein with a $K_D$ less than $10^{-5}$ M.

8. The monoclonal anti-IL-1β antibody or antigen-binding fragment thereof of claim 1, wherein the monoclonal anti-IL-1β antibody or antigen-binding fragment thereof comprises a constant region derived from a human antibody selected from the constant regions of human IgG1, IgG2, IgG3, and IgG4.

9. The monoclonal anti-IL-1β antibody or antigen-binding fragment thereof of claim 1, wherein the monoclonal anti-IL-1β antibody or antigen-binding fragment thereof comprises:
a heavy chain constant region that comprises an Ig gamma-1 chain C region or an Ig gamma-4 chain C region; and a light chain constant region that comprises an Ig kappa chain C region.

10. An antibody-drug conjugate comprising:
the monoclonal anti-IL-1β antibody or antigen-binding fragment thereof of claim 1, and
a drug, wherein the drug is selected from a cytotoxic drug, a tumor chemotherapeutic drug, a nonsteroidal anti-inflammatory drug, colchicine, and a glucocorticoid.

11. A bispecific monoclonal antibody comprising a first protein functional region and a second protein functional region, wherein
the first protein functional region binds to IL-1β, and
the second protein functional region binds to a target that is not IL-1β;
wherein the first protein functional region comprises the monoclonal anti-IL-1β antibody or antigen-binding fragment thereof of claim 1; and
wherein the second protein functional region comprises a monoclonal antibody or antigen-binding fragment thereof.

12. The bispecific monoclonal antibody of claim 11, wherein the first protein functional region is a single chain antibody.

13. An isolated nucleic acid molecule, comprising a nucleic acid sequence encoding the VH of the monoclonal anti-IL-1β antibody or antigen-binding fragment thereof of claim 1.

14. The isolated nucleic acid molecule of claim 13, wherein the isolated nucleic acid molecule comprises at least one of the nucleotide sequences set forth in SEQ ID NO: 1, SEQ ID NO: 5, SEQ ID NO: 9, or SEQ ID NO: 13.

15. An isolated vector, comprising the isolated nucleic acid molecule of claim 13.

16. An isolated host cell, comprising the isolated vector of claim 15.

17. A pharmaceutical composition, comprising the monoclonal anti-IL-1β antibody of antigen-binding fragment thereof of claim 1 and at least one pharmaceutically acceptable carrier or pharmaceutically acceptable excipient.

18. A method of treating rheumatoid arthritis in a subject in need thereof, the method comprising administering to the subject at least one effective amount of the monoclonal anti-IL-1β antibody or antigen-binding fragment thereof of claim 1.

19. The isolated nucleic acid molecule of claim 13, wherein the isolated nucleic acid molecule further comprises a nucleic acid sequence encoding the VL of the monoclonal anti-IL-1β antibody or antigen-binding fragment thereof of claim 1.

20. The isolated nucleic acid molecule of claim 19, wherein the isolated nucleic acid molecule comprises at least one of the nucleotide sequences set forth in SEQ ID NO: 3, SEQ ID NO: 7, SEQ ID NO: 11, and SEQ ID NO: 15.

21. A composition comprising:
a) a first isolated nucleic acid molecule comprising a nucleic acid sequence encoding the VH of the monoclonal anti-IL-1β antibody or antigen-binding fragment thereof of claim 1; and
b) a second isolated nucleic acid molecule comprising a nucleic acid sequence encoding the VL of the monoclonal anti-IL-1β antibody or antigen-binding fragment thereof of claim 1.

* * * * *